(12) United States Patent
Jassawalla et al.

(10) Patent No.: US 6,969,345 B2
(45) Date of Patent: Nov. 29, 2005

(54) MINIATURE, PULSATILE IMPLANTABLE VENTRICULAR ASSIST DEVICES AND METHODS OF CONTROLLING VENTRICULAR ASSIST DEVICES

(75) Inventors: Jal S. Jassawalla, Orinda, CA (US); Phillip J. Miller, Berkeley, CA (US); David H. LaForge, Kensington, CA (US); Tofy Mussivand, Navan (CA)

(73) Assignee: World Heart Corporation, Ontario (CA)

( * ) Notice: Subject to any disclaimer, the term of this patent is extended or adjusted under 35 U.S.C. 154(b) by 0 days.

(21) Appl. No.: 10/729,599

(22) Filed: Dec. 5, 2003

(65) Prior Publication Data

US 2004/0116769 A1 Jun. 17, 2004

Related U.S. Application Data

(60) Provisional application No. 60/431,288, filed on Dec. 6, 2002.

(51) Int. Cl.$^7$ ............................................. A61N 1/362
(52) U.S. Cl. ....................................................... 600/16
(58) Field of Search ...................... 600/16–18; 623/3.1, 623/3.28; 604/6.1–6.14, 122; 156/73.1

(56) References Cited

U.S. PATENT DOCUMENTS

| | | | |
|---|---|---|---|
| 4,427,470 A * | 1/1984 | Kolff | 156/73.1 |
| 4,468,177 A | 8/1984 | Strimling | 417/413 |
| 4,547,911 A | 10/1985 | Strimling | 623/3 |
| 5,511,958 A | 4/1996 | Chen et al. | 417/412 |
| 5,599,173 A | 2/1997 | Chen et al. | 417/412 |
| 5,810,708 A | 9/1998 | Woodard et al. | 600/16 |
| 6,001,056 A | 12/1999 | Jassawalla et al. | 600/16 |
| 6,102,845 A | 8/2000 | Woodard et al. | 600/16 |
| 6,264,601 B1 | 7/2001 | Jassawalla et al. | 600/16 |
| 6,641,558 B1 * | 11/2003 | Aboul-Hosn et al. | 604/122 |

* cited by examiner

Primary Examiner—George Manuel
(74) Attorney, Agent, or Firm—Nixon Peabody LLP

(57) ABSTRACT

A pumping system for assisting either or both ventricles of the heart. In one embodiment, separate devices are provided for each ventricle. In another embodiment, one device provides both right and left pumping. The pumping system is small, efficient, atraumatic, and fully implantable. In addition, the pumping system can provide pulsatile flow during systole. The ventricular assist device includes an actuator plate between a pair of serially connected pumping chambers that operate in a two-stroke mode, specifically a power stroke and a transfer stroke. The ventricular assist device also includes an electromagnetic drive system that provides adjustment to the pump pressure according to the current through an electromagnet. For the pumping system, springs provide a "spring force" on the actuator plate that is towards the high-pressure pump chamber. The bias force allows the springs to store and deliver energy from the electromagnetic drive system to provide better utilization of the pump components, and to reduce the pump size and consumption of electricity.

37 Claims, 20 Drawing Sheets

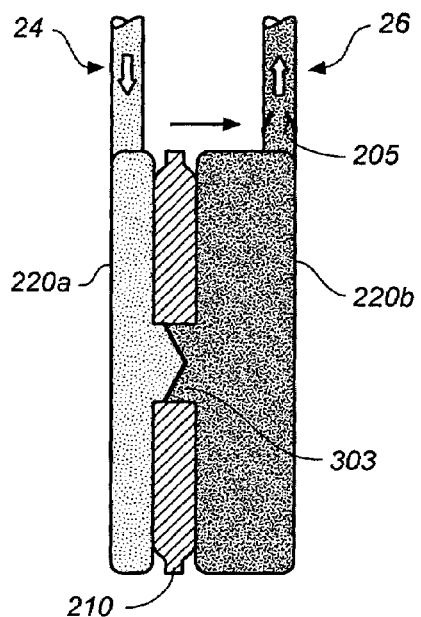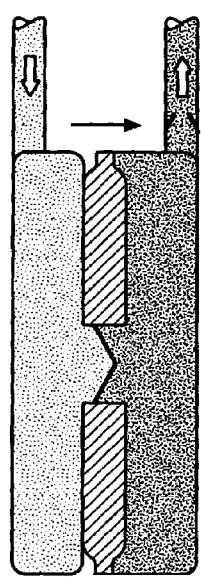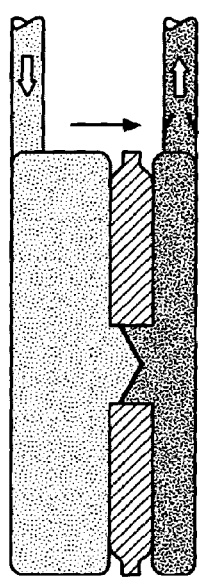
FIG. 7A  FIG. 7B  FIG. 7C
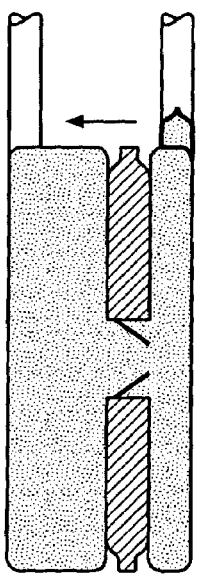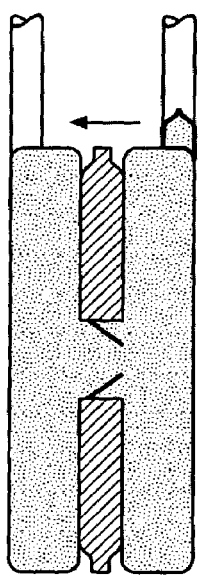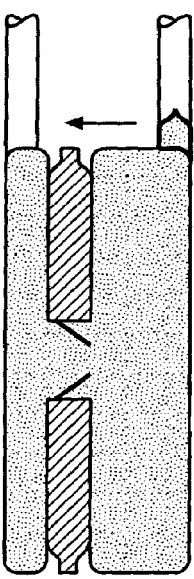
FIG. 7D  FIG. 7E  FIG. 7F

MINIATURE, PULSATILE IMPLANTABLE VENTRICULAR ASSIST DEVICES AND METHODS OF CONTROLLING VENTRICULAR ASSIST DEVICES

CROSS REFERENCE TO RELATED APPLICATION

This application claims the benefit of U.S. Provisional Application No. 60/431,288, filed Dec. 6, 2002, which is incorporated by reference herein.

FIELD OF THE INVENTION

The present invention relates to devices and associated methods for pumping fluids, for example, blood. More particularly, the present invention relates to implantable ventricular assist devices (VADs) that are utilized to replace the function of either the right ventricle or the left ventricle, or both, of the heart. The ventricular assist devices of the present invention include certain features that relate in the art to electric pulsatile devices.

BACKGROUND OF THE INVENTION

Four hundred thousand new cases of congestive heart failure are diagnosed in the United States annually, a number which will only rise in the foreseeable future with the aging of the baby-boom generation. According to the Framingham Heart Study, the five-year mortality rate for patients with congestive heart failure was 75 percent in men and 62 percent in women. Standard medical and surgical therapies benefit only a small percentage of patients with ventricular dysfunction. Potential cardiac transplant recipients with hemodynamic instability may receive temporary mechanical circulatory support, such as an implantable blood pump, as a bridge to cardiac transplantation. Moreover, estimates in the field suggest that 17,000 to 66,000 patients each year in the United States may benefit from a permanent implantable blood pump.

The ventricular assist device (VAD) is a blood pump designed to assist or replace the function of either ventricle, or both ventricles, of the heart. A right ventricular assist device (RVAD) supports pulmonary circulation by receiving or withdrawing blood from the right ventricle and returning it to the pulmonary artery. A left ventricular assist device (LVAD) supports systemic perfusion by receiving or withdrawing blood from the left ventricle (or left atrium) and returning it to the aorta. A biventricular assist device (BVAD) supports both ventricles of the heart. Ventricular assist devices may be either implantable or extracorporeal, with implantable VADs positioned intracorporeally in the anterior abdominal wall or within a body cavity (other than the pericardium) and with extracorporeal VADs located paracorporeally, along the patient's anterior abdominal wall, or externally at the patient's bedside.

The first ventricular assist devices attempted to mimic the pulsating flow of the natural left ventricle by utilizing flexible chambers with volumes approximately equal to the volume of the respective ventricle being assisted. The typical volume of blood expelled by the left ventricle of an adult is between 70–90 ml, but may range from 40–120 ml. The chambers are expanded and contracted, much like a natural ventricle, to alternately receive and expel blood. One way valves at the inlet and outlet ports of the chambers ensured one way flow therethrough.

So-called "pulsatile pumps" may include one or a pair of driven plates for alternately squeezing and expanding flexible chambers. The flexible chambers typically comprise biocompatible segmented polyurethane bags or sacs. The blood sac and drive mechanism are mounted inside a compact housing that is typically implanted in the patient's abdomen. A controller, backup battery, and main battery pack are electrically connected to the drive mechanism. Even the most basic drive mechanisms of the prior art are relatively complex and expensive, and typically incorporate some type of mechanical cam, linkage, or bearing arrangement subject to wear.

Because of the varying volume of the blood sac within the rigid encapsulation housing of pulsatile pumps, accommodation must be made for the air displaced thereby. Some devices utilize a percutaneous tube vented to the atmosphere, which is a simple approach but has the disadvantage of a skin penetration and associated infection risk. Another approach, proposed for fully-implantable VAD systems, is to use a volume compensator. This is a flexible chamber, implanted in the thoracic cavity adjacent to the lungs and communicating with the air space within the housing and outside the blood sac via an interconnecting tube. As the blood sac expands with incoming blood, air is displaced from the housing to the volume compensator. Conversely, expulsion of blood from the blood sac creates a negative pressure within the housing and pulls air from the volume compensator. While eliminating the infection risk of the percutaneous vent, the volume compensator poses certain challenges: increased system complexity, an additional implanted component and potential site of infection, maintaining long-term compliance of the implanted volume compensator sac, problems associated with gas diffusion in or out of the enclosed volume, and problems associated with changes in ambient pressure, such as experienced during a plane flight.

One example of an electric pulsatile blood pump is the Novacor N100 Left Ventricular Assist System (World Heart Inc., Oakland, Calif.). This system contains a single polyurethane blood sac with a nominal stroke volume of 70 ml that is compressed by dual symmetrically opposed pusher plates in synchronization with the natural left ventricle contraction. The pusher plates are actuated by a spring-decoupled solenoid energy converter. The blood pump and energy converter are contained within a housing that is implanted in the patient's abdomen. The N100 employs a percutaneous vent tube that also carries power and control wires.

An example of an electric pulsatile blood pump not requiring external venting is disclosed in U.S. Pat. No. 6,264,601 ("the '601 patent"), incorporated herein by reference. The system of the '601 patent has two pumping chambers formed from two flexible sacs separated by a pusher plate, with the sacs and pusher plate contained within one housing. An electromagnetic drive system acts on an iron armature surrounded by a cylindrically symmetric permanent magnet within the pusher plate to alternatively pump blood through the two sacs by compressing one sac and then the other against the housing. Since each sac contains only fluid that is alternately received and discharged as the pusher plate reciprocates, the total volume of the pump remains constant during pumping and no venting or volume compensator is required. The input and output of each sac includes a one-way valve, providing unidirectional flow that pumps the fluid in a preferred direction. The most efficient use of the electromagnetic drive system is achieved when the power and energy required in each pump stroke is approximately equal.

The '601 patent describes several alternative arrangements for using a blood pump, including a left or right VAD that couples the input and output flows from each chamber in either parallel or series, and a BVAD that separately uses two separate VADs to assist the left and right ventricle. One embodiment described in the '601 patent is a series-displacement pump, in which a first chamber receives a fluid for pumping, and provides that fluid to the input of a second chamber for further pumping ("the '601 series-displacement pump"). In operation, the '601 series displacement pump alternates between a pump stroke and a transfer stroke. When used as a VAD, the pump stroke pumps blood from the second chamber into the aorta while blood is drawn from the ventricle into the first chamber. In the transfer stroke, blood from first chamber is transferred to the second chamber. The fluid connection between the chambers is an external transfer conduit that connects the output of the first sac to the input of the second sac.

The '601 series-displacement pump has several advantages over other prior art pumps including, but not limited to, the ability to provide pulsatile flow, the use of fewer blood conduits and valves, and reduced size. However, the electromagnetic drive system of the '601 patent is optimized for bi-directional use, while the power and transfer strokes of the '601 series-displacement pump each have different power and energy characteristics. While the pump of the '601 patent is capable of operating as a series-displacement pump, there are energy losses that result from not having the drive and pump matched for series operation. Also, in general, the pump of the '601 patent includes a permanent magnet to drive the pusher plates that has a radially symmetric design that is expensive and difficult to manufacture.

Series-displacement pumps generally provide fluid communication between chambers through external conduits. Examples of series-displacement pumps using external conduits include the '601 series-displacement pump, and the pump-driven diaphragm pump and a pusher plate driven pump between two variable-volume chambers as described in U.S. Pat. Nos. 4,468,177 and 4,547,911 to Strimling. The Strimling devices are similar to the '601 pump in that each of the Strimling devices may function either as a BVAD heart pump with each chamber communicating separately with a respective ventricle of the heart, or as a single ventricle-assist pump wherein the two chambers are connected in series with a shunt therebetween.

In recent years there has been increased study into the potential of using rotary pumps (centrifugal or axial) for ventricular assist. These pumps employ fast-moving impellers to impart forward flow to the blood. The impellers are either supported by bearings or are magnetically levitated. A significant advantage of rotary pumps is their relatively compact size and low cost. In addition, the pressure difference maintained by the impeller eliminates the need for one-way valves as in pulsatile pumps. Finally, no venting or volume compensator is necessary.

The use of rotary pumps has generated a significant amount of interest in this field, but as yet many drawbacks prevent general acceptance. For instance, bearing-supported impellers usually require lubrication that must be absolutely kept out of contact with the blood, thus requiring seals that remain highly effective for extended periods. In some designs, the bearings are within the pump housing in contact with blood, which is then used as the lubricating fluid and may be subject to degradation. In addition, the heat generated by some bearing configurations may adversely affect the blood. Some designs eschew bearings altogether and instead utilize magnetically levitated impellers. However, these are relatively complex and sometimes unstable.

A safety issue with rotary pumps is their non-occlusive character, which provides a shunt path for blood regurgitation if the impeller is not rotating. That is, the one-way valves in pulsatile pumps ensure a uni-directional pathway through which blood is propelled, and prevent regurgitation from the arterial vessel if the device shuts off or fails. The natural ventricle can thus function as a back-up perfusion system, bypassing the pump circuit. If the impeller in a rotary pump stops, however, a flow path is created permitting blood from the arterial vessel to be shunted through the pump back into the ventricle, thus seriously impairing the back-up capability of the natural ventricle. To prevent this situation, a one-way valve or occluder of some sort must be provided at the rotary pump outflow. A still further issue with rotary pumps, as yet to be resolved, is the efficacy of the continuous flow of blood provided thereby. There is considerably less experience in the use of long-term circulatory support with continuous flow pumps as opposed to a vast body of experience with pulsatile flow pumps.

In view of the foregoing, there is an ongoing need in the art to improve upon conventional ventricular assist devices, and in particular upon series-displacement pumps. For example, reductions in size and the reduction of weight of the drive units would be advantageous to facilitate full implantation of a device. In addition, it would be advantageous to more closely match the power and operating speeds of pulsatile, series-displacement pumps to provide efficiently use of power over the cardiac cycle while providing pumping during systole. Further, a device that is low in cost but does not have the disadvantages of rotary pumps would be advantageous for long-term use. Accordingly, there remains a need in the art for a small, efficient, atraumatic, and fully implantable series-displacement ventricular assist device that overcomes the deficiencies of conventional devices.

Therefore, it is one aspect of the present invention to provide a ventricular assist device that is smaller, more robust and more efficient than prior art ventricular assist devices.

It is another aspect of the present invention to provide a ventricular assist device driven by an electromagnetic device at physiological speeds with high pump efficiency.

It is one aspect of the present invention to provide an electromagnetic drive useful for a ventricular assist device that has constant force characteristics, and that produces a pressure under rest conditions.

It is yet another aspect of the present invention to provide an electromagnetic drive useful for a ventricular assist device that produces a force that varies approximately linear with the coil current of the drive.

It is yet another aspect of the present invention to provide an electromagnetic drive useful for a ventricular assist device that can be easily controlled to produce desired output pressures.

It is another aspect of the present invention to provide a ventricular assist device that nominally beats once per heart beat using an electromagnetic drive that is optimized for efficiency and weight.

SUMMARY OF THE INVENTION

The present invention provides a pumping system for assisting one or both ventricles of the heart. The pumping system of the invention has a relatively small size and is free of many disadvantages inherent in conventional blood pumps. In addition, the pumping system of the present invention can provide pulsatile flow during systole. Accordingly, the present invention provides a pumping system that is small, efficient, atraumatic, and fully implantable while overcoming the deficiencies of conventional devices.

In accordance with one aspect of the present invention, a ventricular assist device is provided having a blood pump with an electromagnetic drive that uses springs to produce a constant force biased towards the high pressure side of the pump.

In accordance with another aspect of the present invention, a ventricular assist device is provided that has a pair of variable-volume chambers situated on either side of an actuator plate having an internal transfer valve therethrough.

In accordance with yet another aspect of the present invention, a ventricular assist device is provided that pumps nominally once per cardiac cycle and that dynamically ejects blood at the end of a power stroke, thus reducing the required size of the pumping chambers.

In accordance with one aspect of the present invention, a ventricular assist device is provided having an actuator plate between a pair of serially connected pumping chambers that includes a spring bias for pre-pressurizing a pumping chamber.

In accordance with yet another aspect of the present invention, a ventricular assist device is provided that can be used for either right or left ventricular assist.

In accordance with yet another aspect of the present invention, a ventricular assist device is provided that can be used for right and left ventricular assist. In one embodiment, separate devices are provided for each ventricle. In another embodiment, a ventricular assist device is provided that can be used for both right and left ventricular assist with one device.

In accordance with one aspect of an embodiment of the present invention, a bias force and energy storage device are provided to allow the drive unit to be used at a nearly constant power level while providing a higher output pressure to the systemic circulation.

In accordance with another aspect of the present invention, a ventricular assist device is provided having an actuator plate (also referred to herein as a "pusher plate") between a pair of serially connected pumping chambers that operate in a two-stroke mode, specifically a power stroke and a transfer stroke, and which includes a spring bias for storing energy from a drive unit during the transfer stroke to augment the pressure generated during the power stroke.

In accordance with yet another aspect of the present invention, a ventricular assist device is provided having an actuator plate between a pair of serially connected pumping chambers that includes a spring for suspending the actuator plate between the chambers and stabilizing the plate from tilting forces.

In accordance with one aspect of the present invention, a ventricular assist device is provided that triggers pumping based on contracting of the ventricle. In one embodiment, triggering is based on sensing of the ventricular pressure. In another embodiment, triggering is based on the motion of an element internal to the pump.

In accordance with yet another aspect of the present invention, a ventricular assist device is provided having an electromagnetic drive that provides adjustment to the pump pressure according to the current through an electromagnet. In one embodiment, the force is biased towards a high pressure portion of the pump.

In accordance with yet another aspect of the present invention, a ventricular assist device is provided having an electromagnetic drive that provides adjustment to the pump pressure according to the current through an electromagnet. In one embodiment, the force is proportional to the coil current and is approximately independent of the position of a pump actuator.

In accordance with one aspect of the present invention, a ventricular assist device is provided having an electromagnetic drive with multiple sensors for controlling pump operation.

In accordance with yet another aspect of the present invention, a method for controlling a ventricular assist device provides for initiation of the device as a function of changes in ventricular pressure.

In accordance with another aspect of the present invention, a ventricular assist device is provided by a pump having a frame formed from a soft magnetic material and a pair of compressible chambers connected in series and disposed in the frame. The pair of compressible chambers includes a first chamber connected to the device inlet and a second chamber connected to the device outlet. The device also includes an armature and a one-way valve. The armature is disposed between each of the pair of compressible chambers and movable within the frame to simultaneously contract one of the pair of chambers and expand the other of the pair of chambers. The one-way valve provides fluid communication between the pair of chambers in a direction from said first chamber to said second chamber. The motion of the armature towards said first chamber transfers a fluid within the first chamber to the second chamber. The motion of the armature towards the second chamber fills the first chamber from the inlet and empties said second chamber into the outlet. The device also includes an electromagnetic drive disposed within the frame and adapted to alternately force the armature against one and the other of the pair of compressible chambers. In one embodiment, a second one-way valve is provided at the outlet of the second chamber.

In accordance with yet another aspect of the present invention, a ventricular assist device is provided by a pump having a frame formed from a soft magnetic material and a pair of compressible chambers connected in series and disposed in the frame. The pair of compressible chambers includes a first chamber connected to the device inlet and a second chamber connected to the device outlet. The device also includes an armature, a one-way valve, and a drive unit. The armature is disposed between each of the pair of compressible chambers and movable within the frame to simultaneously contract one of the pair of chambers and expand the other of the pair of chambers. The one-way valve provides fluid communication between the pair of chambers in a direction from the first chamber to the second chamber, where the motion of the armature towards said first chamber is a transfer stroke that transfers a fluid within the first chamber to the second chamber, and where the motion of the armature towards the second chamber is a power stroke that fills the first chamber from the inlet and empties the second chamber into the outlet. The drive unit includes an electromagnetic drive disposed within the frame and an energy storage element disposed between the frame and the armature. During the transfer stroke, electric power delivered to the electromagnetic drive is stored in the energy storage element, and during the power stroke, electric power delivered to the electromagnetic drive and the stored energy is delivered to the armature. In one embodiment, a second one-way valve is provided at the outlet of the second chamber.

In accordance with one aspect of the present invention, an electromagnetic drive is provided having one or more magnets arranged about a common axis.

In accordance with another aspect of the present invention, an electromagnetic drive is provided having springs for counterbalancing the attraction of magnets in an armature to the metal of a frame. In one embodiment, the counterbalancing provides a drive that, in the absence of an applied current, has a bias force that is approximately independent of armature position. According to another embodiment, the force produced by the drive is proportional to the applied current and approximately independent of the armature position.

In accordance with yet another aspect of the present invention, a electromagnetic drive is provided by a device having a frame formed from a soft magnetic material; one or more coils disposed within the frame that, when electrically energized, generate a magnetic flux and define one or more pairs of magnetic poles each having a polar axis; an armature within the frame having a magnetic core, a non-magnetic material surrounding the core, and one or more magnets in the non-magnetic material, wherein the core is movable along the polar axis, and where the poles of the one or more magnets are oriented perpendicular to the polar axis with like oriented pole aligned towards the polar axis; and one or more springs positioned between the frame and the armature so as to exert a spring force on the armature; wherein one or more magnets generate a magnet force on the armature resulting from the attraction of the magnet to the frame when the pair of coils is not electrically energized, wherein the sum of the spring forces and the magnetic force is a net bias force that is approximately independent of the position of the armature along the polar axis and biases the armature towards one of the pair of poles, and wherein the energized coils generate a coil force on the armature that is approximately independent of the position of the armature along the polar axis and that varies according to the degree of energization of the coils.

In accordance with yet another aspect of the present invention, a ventricular assist device is provided by a device including a blood pump connected to a heart and adapted to pump blood from the ventricle to the aorta, a drive system to supply power to the pump, a sensor adapted to detect responses increases in the ventricular pressure; and a controller for actuating the blood pump upon sensing an increase in the ventricular pressure.

Broadly stated, the present invention provides a ventricular assist device for pumping blood between an inlet and an outlet, the device comprising: a frame; a pair of compressible chambers disposed within the frame, the pair of compressible chambers including a first chamber connected to the inlet and a second chamber connected to the outlet; an actuator disposed between the pair of compressible chambers and movable therebetween, where the movement of the actuator increases the volume of one of the pair of compressible chambers and decreases the volume of the other of the pair of compressible chambers; and a one-way valve for providing fluid communication from the first chamber to the second chamber; and a drive unit adapted to alternately move the actuator towards one or the other of the pair of compressible chambers, wherein the movement of the actuator towards the first chamber is a transfer stroke that transfers a fluid within the first chamber to the second chamber, and wherein the movement of the actuator towards the second chamber is a pump stroke that fills the first chamber from the inlet and empties the second chamber into the outlet.

A further understanding of the invention can be had from the detailed discussion of the specific embodiments below. It is therefore intended that the invention not be limited by the discussion of specific embodiments.

Additional objects, advantages, aspects and features of the present invention will become apparent from the description of embodiments set forth below.

BRIEF DESCRIPTION OF THE DRAWINGS

The foregoing aspects and the attendant advantages of the present invention will become more readily appreciated by reference to the following detailed description, when taken in conjunction with the accompanying drawings, wherein:

FIGS. 7A to 7F are schematic views of one configuration of pumping chambers of the present invention;

Reference symbols are used in the Figures to indicate certain components, aspects or features shown therein, with reference symbols common to more than one Figure indicating like components, aspects or features shown therein.

DETAILED DESCRIPTION OF THE INVENTION

Figure 1A:
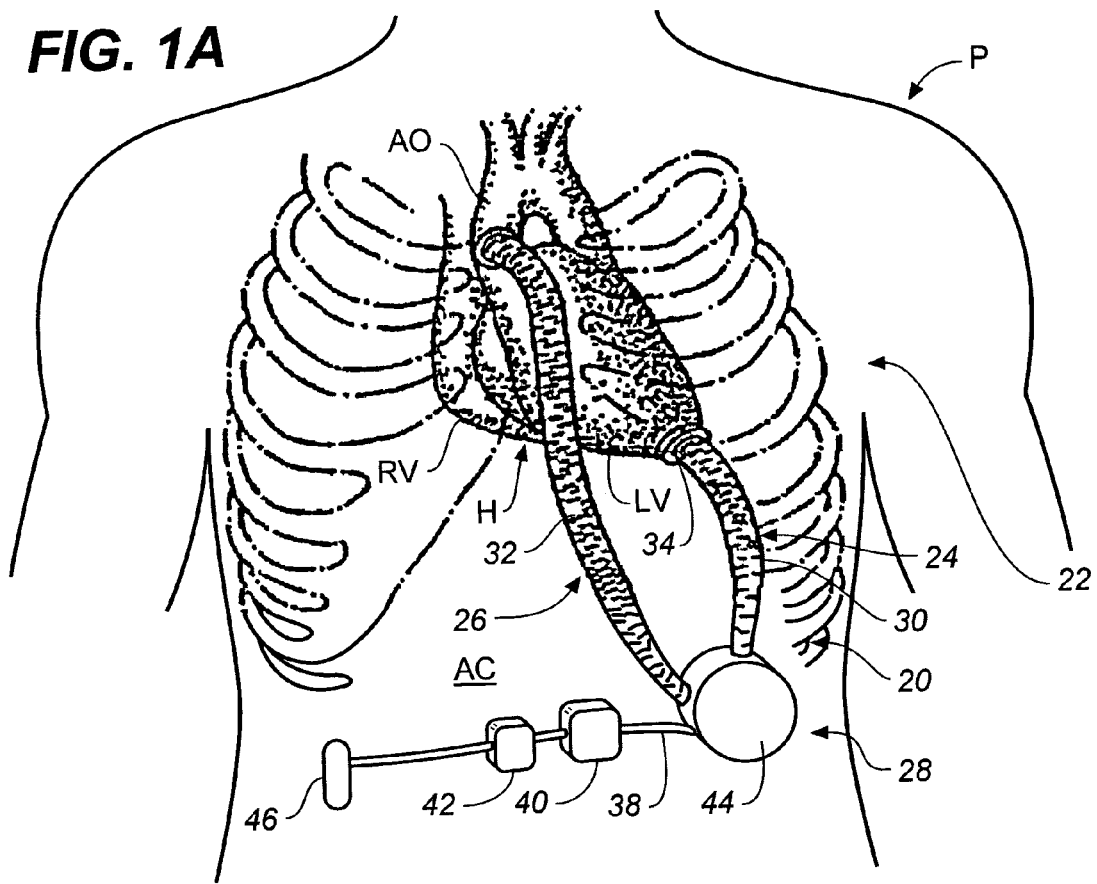
FIG. 1A is a perspective view of a ventricular assist system of the present invention connected to a heart of a patient for left ventricular assist.

With reference first to FIG. 1A, a perspective view of a ventricular assist system 22 of the present invention is shown connected to a heart H of a patient P for the assist of a left ventricular LV. FIG. 1A shows a living human host patient P in fragmentary front elevation view, and with parts of the patient's anatomy shown in phantom or removed solely for better illustration of the salient features of the present invention. A pumping portion 20 of ventricular assist system 22 is surgically implanted into the patient's abdominal cavity AC and connected to the heart H with cannulation. The cannulation includes an inlet conduit 24 communicating blood from the patient's left ventricle LV into the pumping portion 20, and an outlet conduit 26 communicating blood from the pump 20 to the patient's aorta AO. The pumping portion 20 of ventricular assist system 22 may also be implanted in the chest cavity of the patient with similar cannulation to the LV and the patient's aorta.

For purposes of explanation and without limiting the scope of the present invention, ventricular assist system 22 is illustrated assisting the left ventricle LV of the heart of the patient P. In addition to being configurable as a left ventricular assist device (LVAD), the ventricular assist system 22 may also be configured to assist the right ventricle (RVAD). Therefore, as a general matter, and except in reference to the illustrated LVAD, the source of blood for the ventricular assist system 22 may be termed the "assisted ventricle," while the destination of the pressurized blood will be designated the "arterial vessel."

Each of the conduits 24 and 26 include segments 30 and 32 extending to the left ventricle LV and aorta AO, respectively. Segment 30 and 32 are preferably flexible, and segment 30 is alternatively a rigid segment. The inlet and outlet conduits 24 and 26 are attached to the natural tissue of the ventricle and the arterial vessel by sutures to establish and maintain blood flow, and may include appropriate structure for this purpose such as a sewing ring 34 for ventricular attachment. In any of the contemplated configurations of LVAD or RVAD, the inlet conduits are anastomosed to the respective ventricle, while the outlet conduits are anastomosed to the appropriate arterial vessel, which for left ventricular assist is typically the aorta AO and for right ventricular assist is typically the pulmonary artery. As will be explained below, the ventricular assist system 22 includes a single ventricular anastomosis providing blood to input ports in the pumping portion 20. Details of the conduits 24, 26 may be shown and described in U.S. Pat. No. 6,001,056, the disclosure of which is expressly incorporated herein by reference.

With continued reference to FIG. 1A, a power cable 38 extends from the pumping portion 20 to a controller 40, a power supply 42, such as a battery pack, and a energy transfer unit 46, such as a transcutaneous, inductively coupled transformer, to provide energy to recharge the power supply from a source (not shown) that is external to the body of patient P. Other means for powering the ventricular assist system 22 are known which require a cable through the skin, and the present invention is not so limited. In addition, controller 40 and power supply 42 may be combined into a single implantable unit.

Figure 1B:
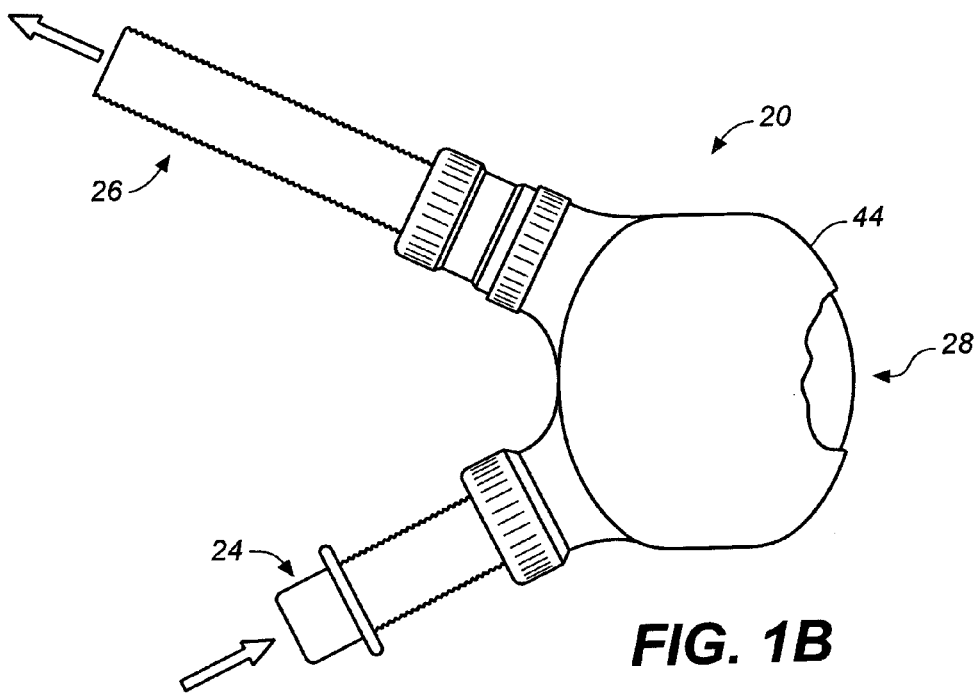
FIG. 1B is top view of the pumping portion of the present invention including a cut-way showing the blood pump.

With reference to FIG. 1B, a top view of pumping portion 20 has a cut-way portion showing that the pumping portion includes a housing 44 that covers a blood pump 28. Housing 44 is preferably rigid and is outwardly formed of a biocompatible coating such as a polymer or other suitable biocompatible material.

The description that follows will begin with a detailed discussion of the blood contacting, fluid moving portions of pump 28, followed with details of the fluid moving aspects of the pump, and then by details of the suspension and drive aspects of the pump. The operation of the integrated system will then be presented, followed by alternative integrated pumps. Further disclosure of the various embodiments is to be found in Appendix A, attached hereto.

Figure 2:
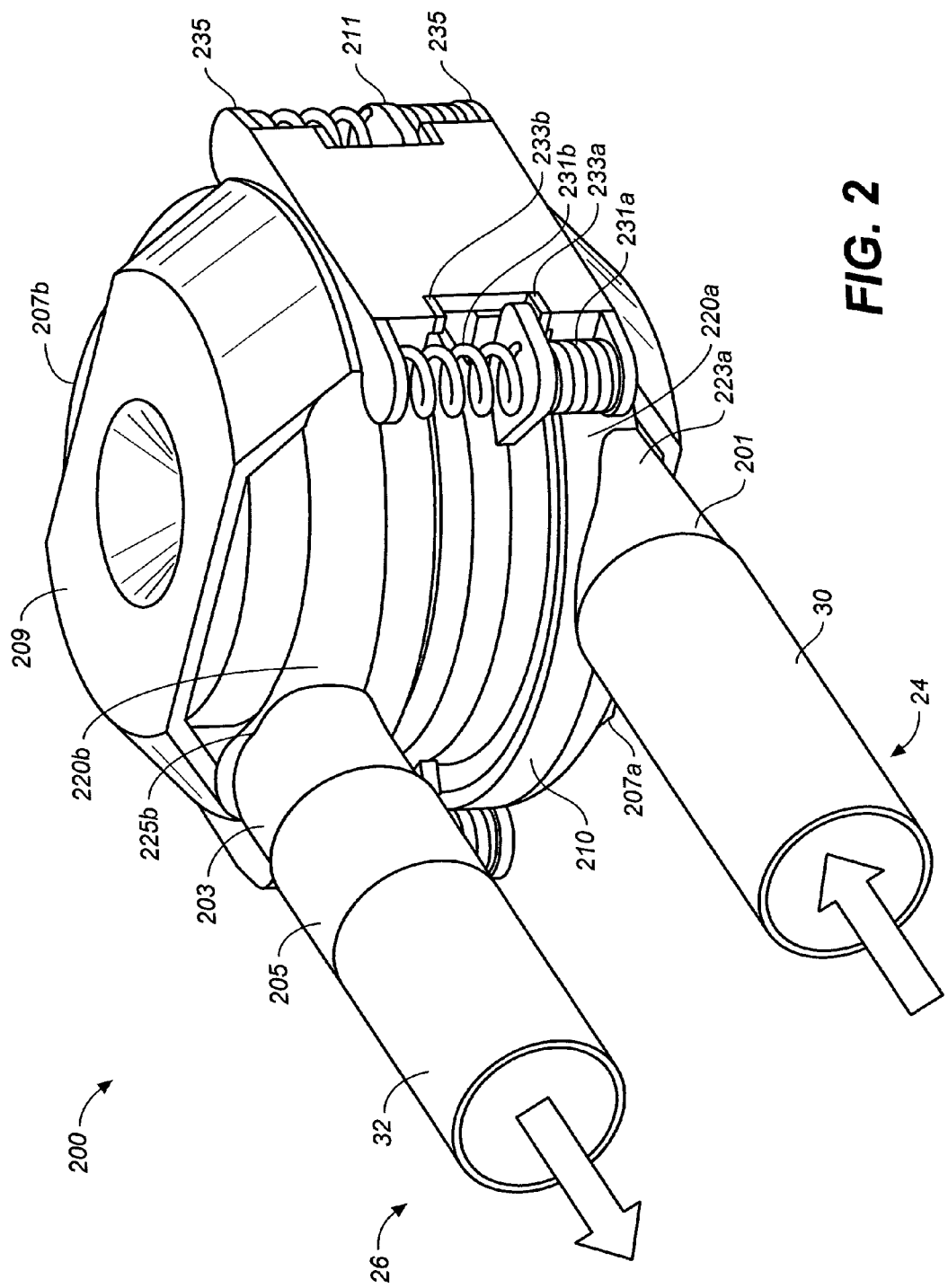
FIG. 2 is a perspective view of the first embodiment blood pump of the invention.
Figure 3:
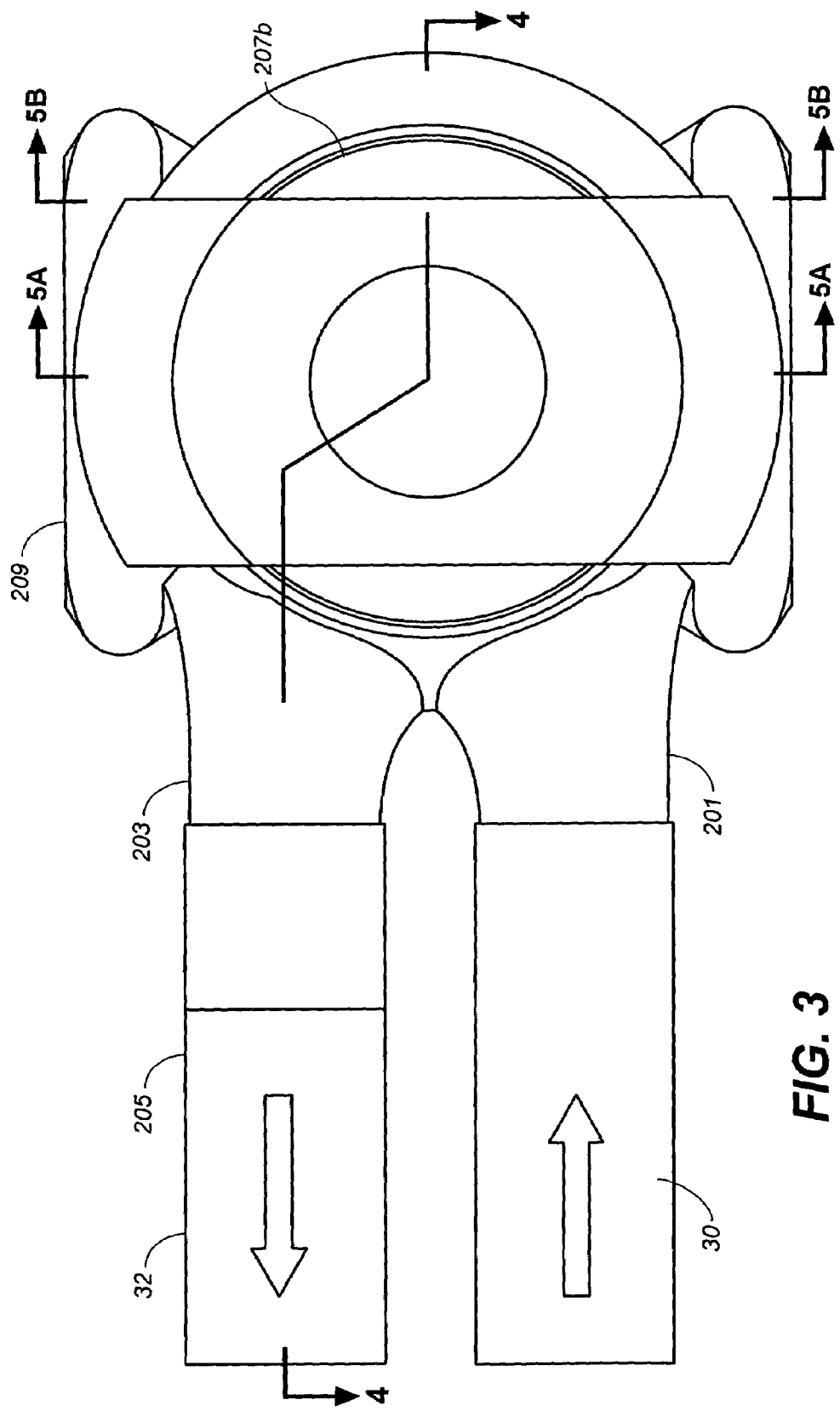
FIG. 3 is a top view of a first embodiment blood pump of the invention.

A first embodiment of a blood pump 200 of system 22 is seen in greater detail in FIGS. 2–5, 6A and 7 with housing 44 removed, in which FIG. 2 is a perspective view and FIG. 3 is a top view of the pump, and FIGS. 4–6A and 7 are various sectional views. With reference to the perspective view of FIG. 2, blood pump 200 is connected to conduits 24 and 26, which receive and provide blood, respectively, during pumping. Pump 200 includes an inlet portion 201, an outlet portion 203, and a valve 205. More particularly, the flexible segment 30 connects to inlet port 201 and flexible segment 32 connects outlet portion 203 that includes valve 205.

As will be described below, the pump 200 includes a pair of variable-volume chambers contained within housing 44 and operating in synchronization to provide a positive-displacement pump. The arrows in FIGS. 2–4 indicate the direction of the flow through a pumping system 22. Specifically, the flow enters pump 200 through conduit 24 into inlet portion 201, and exits the pump at outlet portion 203 and through valve 205 into conduit 26. Valve 205 is a unidirectional flow valve, as described below, that provides flow generally in the direction indicated by the arrows of FIGS. 2–4.

Figure 4:
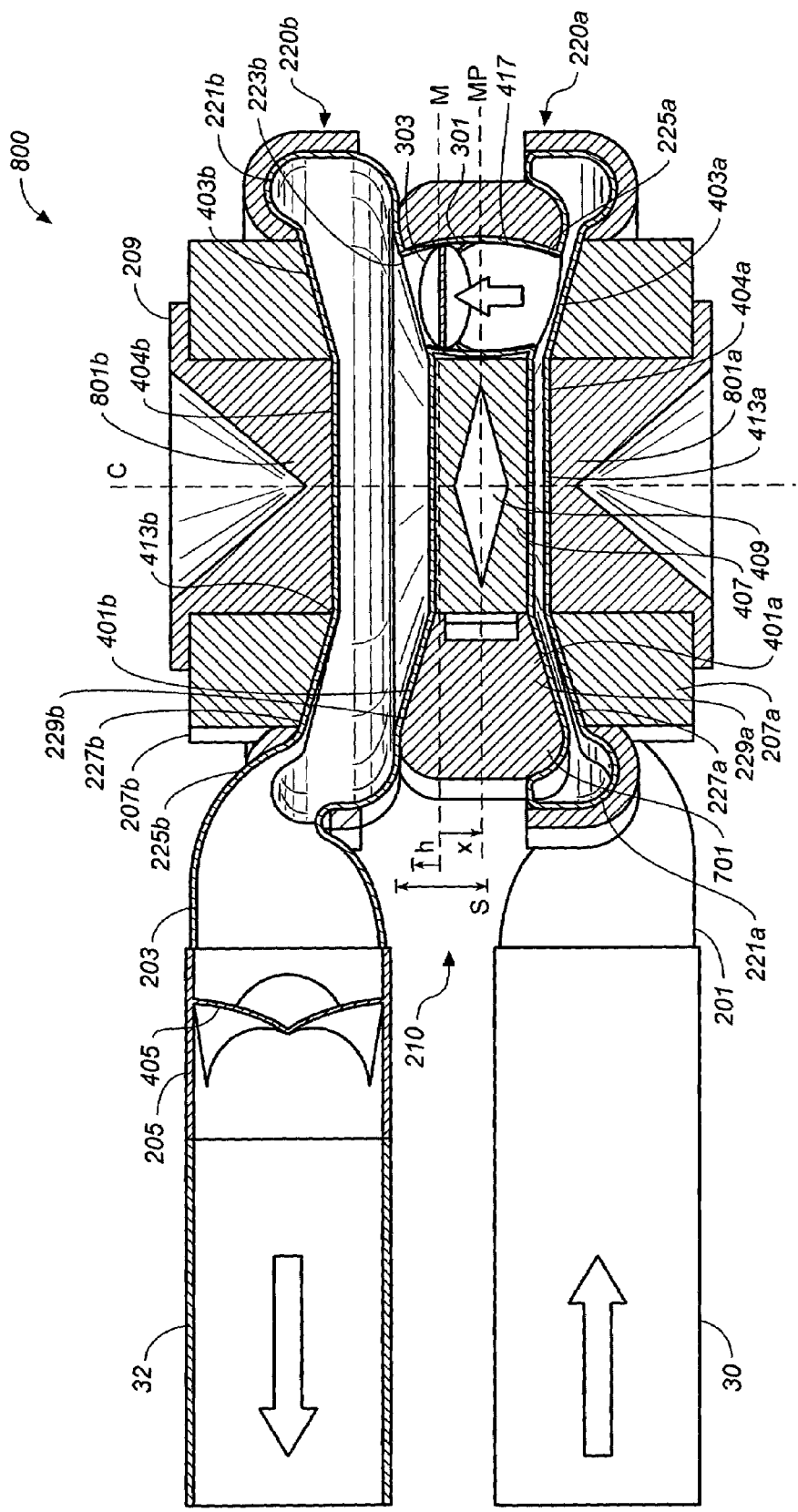
FIG. 4 is a sectional view of the first embodiment blood pump of the invention taken along line 4—4 of FIG. 3.

With further reference to the embodiments shown in FIGS. 2 and 4, pump 200 includes a pair of variable-volume chambers 220, an armature or actuator plate, 210 having actuator surfaces 401, a frame 209 partly enclosing the chambers and actuator plate and retaining a pair of coils 207, and four pairs of springs 231. Pump 200 also includes an electromagnetic structure 800 powered by coils 207 as shown with reference to FIG. 8, and described subsequently. As such pump 200 is conveniently discussed with regards to a center, or polar, axis C through the center of coils 207 and a midplane M between coils 207, both of which are shown in FIGS. 4 and 8. Importantly, the movement of armature 210 within frame 209 affects changes in the volume of chambers 220. In the embodiment of pump 200, the volumes are changed through the contact of chambers 220 with actuator surfaces 401 of armature 210, and with frame 209 and coils 207, though the scope of the present invention is not limited by this structure. Since armature 210 can move within frame 209 to actuate a change in volume of chambers 220 it is alternatively referred to herein as either an "actuator plate" or an "armature." While actuator plate 210 surrounds the electromagnetic structure of armature 210, the present invention is not so limited. More generally, pump 28 provides pumping action through the interaction of a pair of variable-volume chambers and an electromagnetic structure having an armature, and the actuator plate does not necessarily surround the electromagnetic structure of the armature. In an alternate embodiment (not shown) the actuator plate is not surrounded by the electromagnetic structure of the armature, instead the armature is coupled to the actuator plate.

As is shown in FIGS. 2 and 4, frame 209 is a box-like structure that includes a pair of inward facing surfaces 413 (413a, 413b), four pairs of surfaces 235 and four pairs actuator plate stops 233. Frame 209 is part of electromagnetic structure 800 as is discussed below, and as such is formed from a soft magnetic material. The box-like structure allows frame 209 to provide these functions while minimizing the weight of pump 200. Coils 207 are retained in frame 209 and present inward facing surfaces 403 (403a, 403b). Surfaces 403 and 413 together form inward facing surfaces 404. Specifically, surface 403a and 413b together define surface 404a, and surface 403b and 413b together define surface 404b.

As shown best in FIG. 4, the pair of chambers 220 includes a first, or transfer, chamber 220a and a second, or pump, chamber 220b. As shown in the Figures, common features of the pair of chambers 220 are indicated with the ending "a" or "b" for the first or second chamber, respectively. Specifically, each of the pair of chambers 220 (220a, 220b) includes a flexible sac 221 (221a, 221b), the internal volume of which defines a chamber volume, and a pair of ports 223 (223a, 223b) and 225 (225a, 225b) to the internal volume. In addition, each of the pair of chambers 220 has an outwardly facing surface 227 (227a, 227b) and an inwardly facing surface 229 (229a, 229b). Inward surfaces 404 are adjacent to corresponding ones of the outwardly facing surfaces 227 and provide support for chambers 220. Fluid inlets and outlets to chambers 220 are provided at inlet portion 201, which is connected to port 223a, and at outlet portion 203, which is connected to port 225b. Fluid communication between each of the pairs of chambers 220 are provided by a transfer portion 301. As is best seen in FIGS. 4 and 5B, transfer portion 301 connects chambers 220 at ports 225a and 223b, and has an internal transfer valve 303.

Each of the pair of flexible sacs 221 are preferably configured as relatively flat disk-shaped bags. It should be noted that other sac configurations are possible within the understanding of one skilled in the art, and also that variable-volume chambers may be defined by structures other than flexible sacs, such as piston-cylinder couples, moveable walls, etc. A number of features of the present invention can thus be transferred to other fluid propulsion arrangements, though the use of dual flexible sacs provides a number of significant advantages and is thus preferred.

Figure 5A:
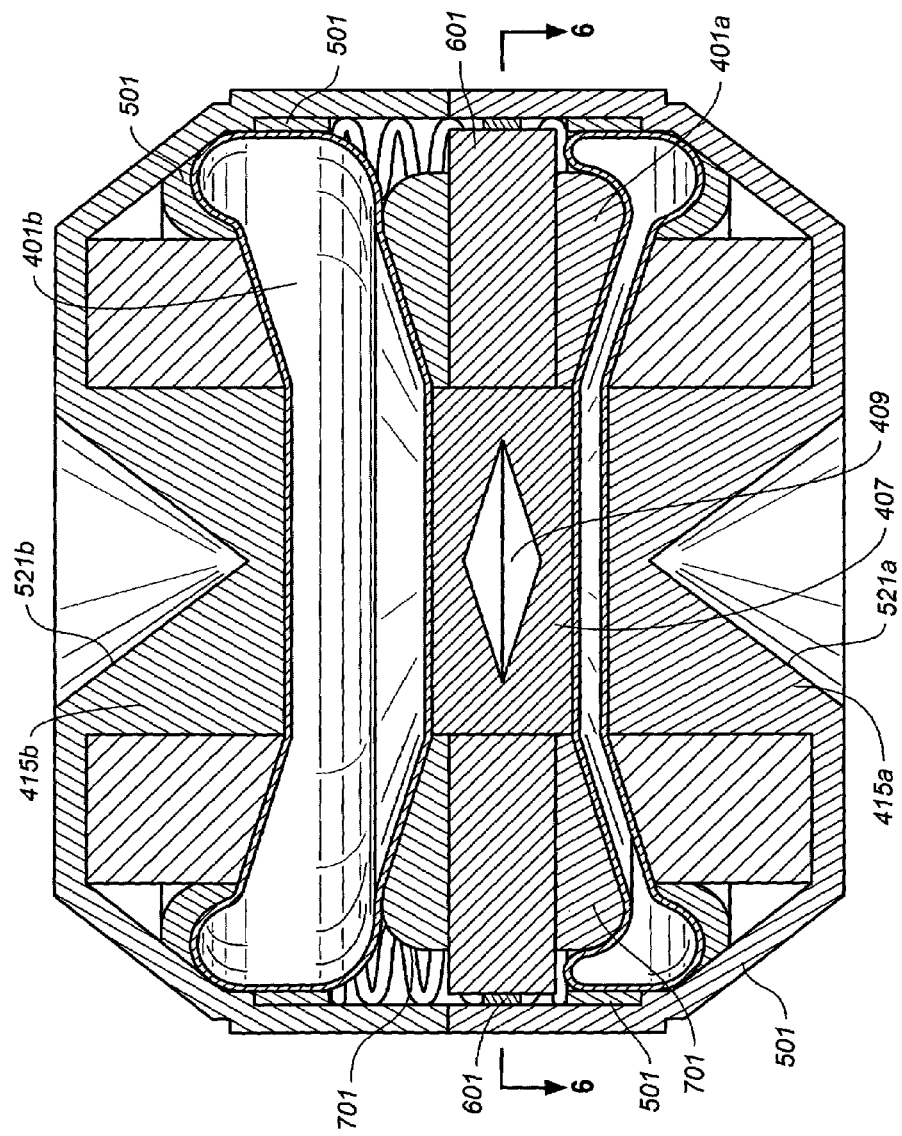
FIG. 5A is a sectional view of the first embodiment blood pump of the invention taken through the magnets along line 5A—5A of FIG. 3.
Figure 5B:
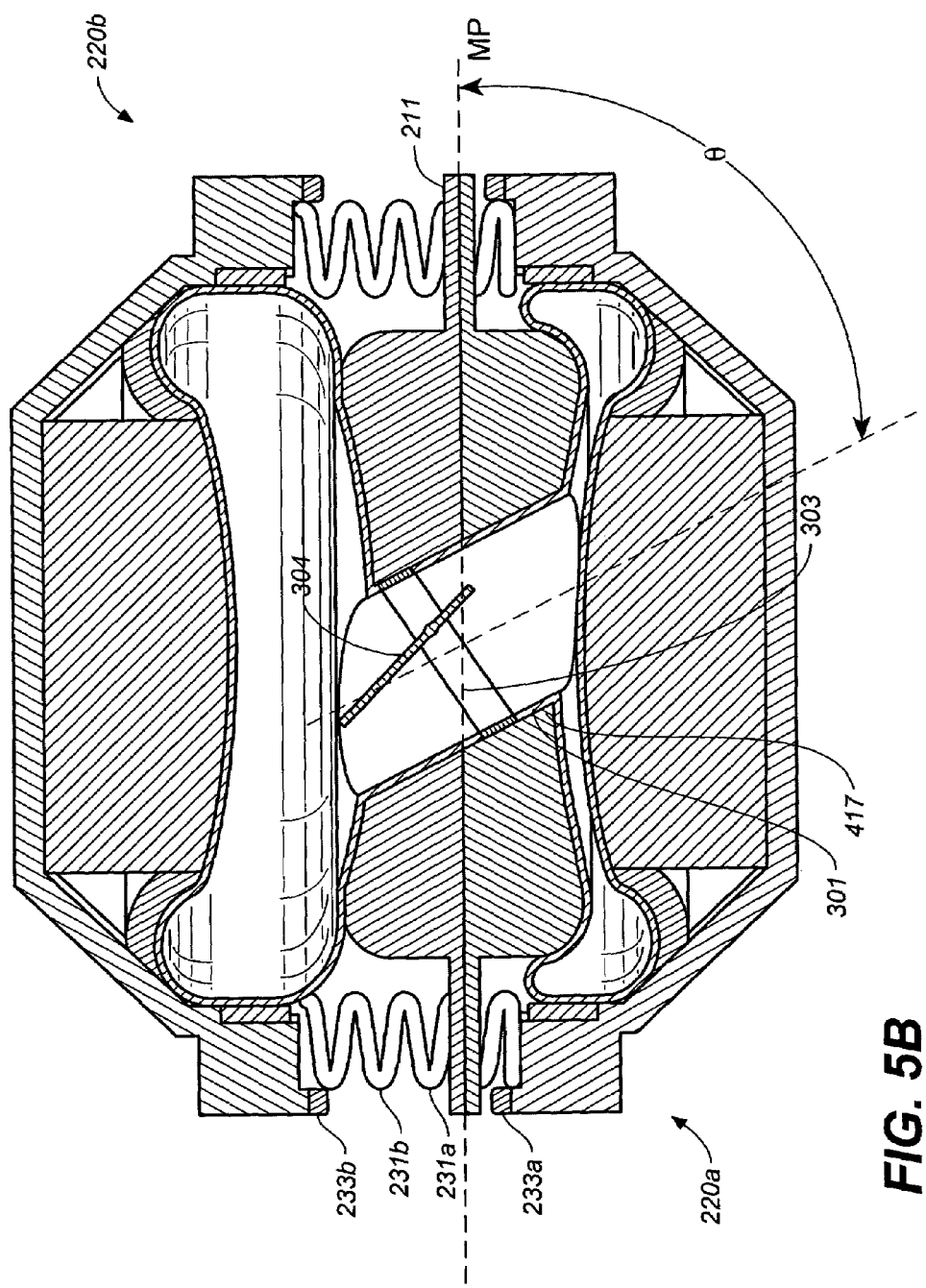
FIG. 5B is a sectional view of the first embodiment blood pump of the invention taken through the internal transfer portion along line 5B—5B of FIG. 3.
Figure 6B:
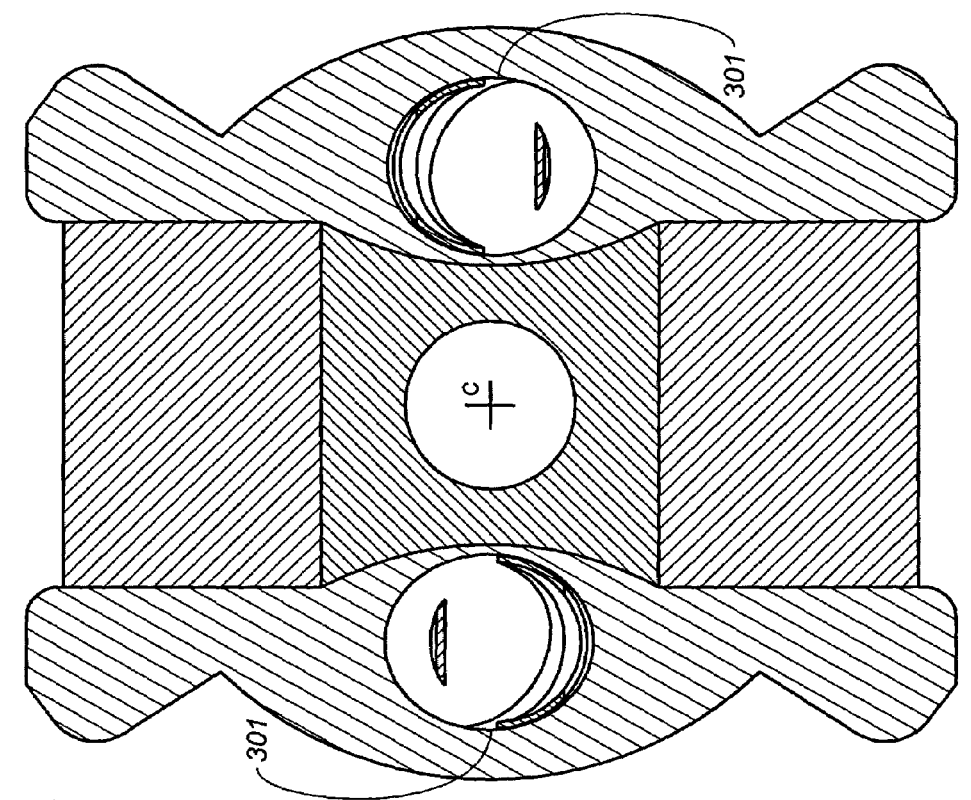
FIG. 6B is a sectional view of an alternative embodiment actuator plate having two transfer ports and taken along line 6—6 of FIG. 5A.
Figure 6A:
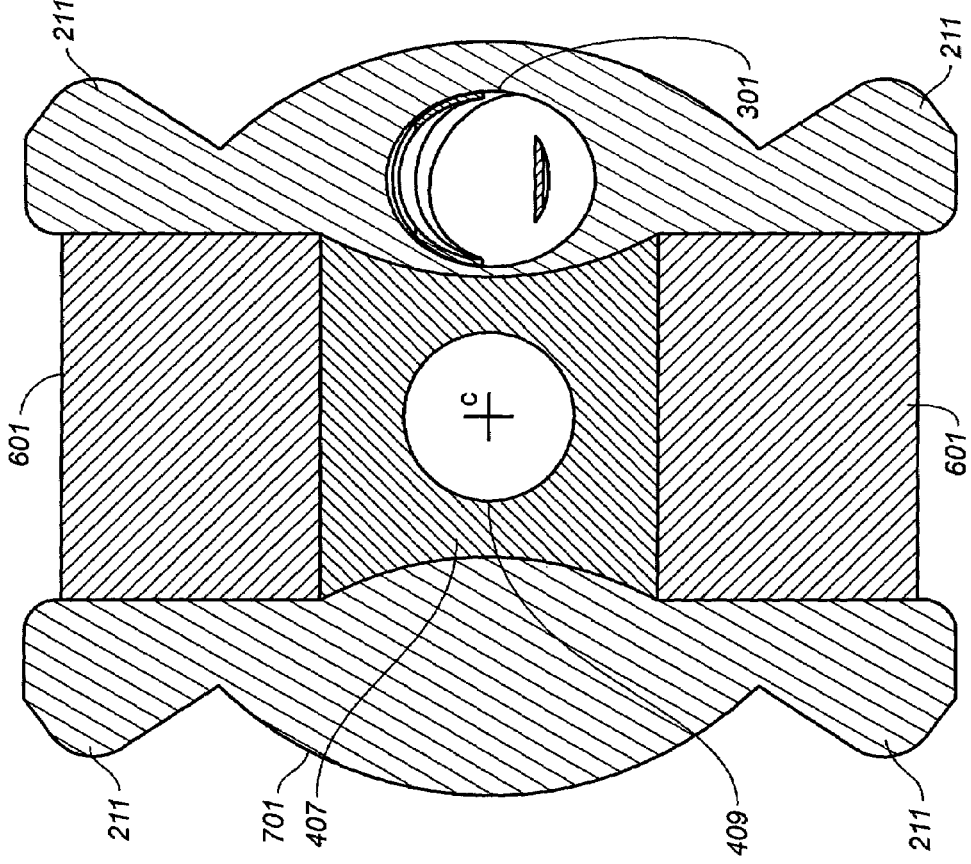
FIG. 6A is a sectional view of the actuator plate of the first embodiment blood pump of the present invention taken along line 6—6 of FIG. 5A.

With reference to FIGS. 4, 5A and 6A, actuator plate 210 is a generally planar structure having the pair of spaced apart, outer actuator surfaces 401 (shown as 401a and 401b) and four tabs 211 that are disposed about the actuator plate. Preferably, the tabs are arranged equidistant from and symmetrically disposed about the actuator. Actuator plate 210 is positioned within frame 209 such that tabs 211 can move in a direction generally aligned with and perpendicular to center axis C and between actuator plate stops 233. Actuator plate 210 also has a passageway 417 through which transfer portion 301 passes from chamber 220a to 220b.

With further reference to FIG. 4, the pair of chambers 220 is disposed on either side of actuator plate 210 and within frame 209. Specifically, the pair of sacs 221 are disposed in parallel and spaced apart by actuator plate 210, with actuator surface 401a of the actuator plate contacting inwardly facing surface 229a of first sac 221a, and actuator surface 401b of the actuator plate contacting inwardly facing surface 229b of second sac 221b. The outward facing surfaces 227 of sacs 221 are also in contact with corresponding ones of inward facing surfaces 404. The inwardly-facing surfaces 229 and the outwardly facing surface 227 of each sac 221 are preferably affixed to actuator plate 210 and surfaces 404 with, for example, adhesive. With further reference to FIG. 5A, pump 28 of the present invention may include plastic housing rings 501 disposed between sacs 221 and frame 209 to provide additional support to sacs 221, and to direct movement of the sacs during pumping to preferred portions of the sacs, for example, those areas that are adjacent to but not in contact with actuator plate 210.

Each one of spring 231 spans the distance from one side of one of tabs 211 to one of surfaces 235. Pump 200 thus provides for the suspension of actuator plate 210 within frame 209 by pairs of springs 231. As described below, the suspension of actuator plate 210 by springs 231 stabilizes the motion of the actuator plate in frame 209, in that tilting of the plate during this motion is corrected by the righting force of springs 231. In addition to suspending actuator plate 210 within frame 209, springs 231 are used to store and release energy to the drive, as discussed subsequently. The position of actuator plate 210 within frame 209 is conveniently discussed with reference to a distance indicated as x representing a displacement of a midplane MP of the actuator plate 210, as shown in FIGS. 4 and 8. Actuator plate 210 has a maximum travel of $x = S/2$ on either side of midplane M. Since the pump has room for sacs 221 and blood between the actuator plate 210 and frame 209, the maximum travel $S/2$ is less than the gap g.

Movement of actuator plate 210 within frame 209 deforms and changes the volume of individual ones of the pair of chambers 220. However, the total volume of the pair of chambers 220 remains constant as the actuator plate moves due to the attachment of chambers 220 to both frame 209 and actuator plate 210. The ejection volume of each of the chambers 220 is no more, and preferably less than, the ejection volume of the ventricle being assisted. For example, in the illustrated pump of FIG. 2, the ejection volume of each of the chambers 220 is on the order of the ejection volume of the left ventricle LV shown in FIG. 1A. The ejection volume of each of the chambers 220 is preferably less than the expected ejection volume of ejected blood, for example from 40 to 60 ml. To accept and pump the ejection volume of the ventricle in full with chambers 220, the blood pump 28 has a drive system that nominally pumps the chambers 220 once for each beat of the heart H and provides a flow of blood during such pumping. The drive system displaces the armature 210 to alternately compress each of the pair of chambers 220. The range of motion of armature 210, and thus the minimum and maximum volumes of chambers 220 is determined by surfaces 235, or preferably by the placement of stops 233, which both control the stroke range of pump 200 and provide damping in case of excessive armature motion.

Each of the inlet and outlet conduits 24, 26 extend generally tangentially from the cylindrical pumping portion 20, as is best seen in FIGS. 2 and 3. The configuration of ports 225a and 225b are disposed tangentially with respect to the disk-shaped sacs 221a and 221b. Likewise, ports 223a and 223b are tangential to the sacs 221a and 221b. The tangential orientation of the ports 223 and 225 is believed to most effectively fill and flush blood to and from the chambers 220. The housing 44 also includes apertures (not shown) for receiving ports 223 and 225 that are sealed about the ports to prevent fluid seepage therebetween. Details of various aspects of the sac shape, connectors and seals are shown and described in U.S. Pat. No. 5,511,958, the disclosure of which is expressly incorporated herein by reference.

The shape of the chambers 220 during the movement of actuator plate 210 within frame 209 is given by the limits of actuator plate motion imposed by tabs 211 and actuator plate stops 233, and the shape of the surfaces to which it is attached, specifically the matching surfaces 404a and 401a of sac 221a, and surfaces 404b and 401b of sac 221b. Preferably, the volumes defined by sacs 221 also facilitate the filling and flushing of blood, and avoid fully compressing the volumes and possibly damaging blood therein. As described below, several of these surfaces also perform functions associated with the electromagnetic drive, and thus necessarily have magnetic properties described below. Additional material required to shape surfaces 401a, 401b, and 404 to achieve proper flow through pump 200 may thus be provided through the use of suitable non-magnetic materials. It is preferable that these materials are light weight, and thus appropriate materials include, but are not limited to plastics, epoxies, or lightweight nonmagnetic metals, such as aluminum.

As seen in FIG. 4, outlet portion 203 includes valve 205 having a flap structure 405 and transfer portion 301 includes valve 303. The valves 205 and 303 enable the positive-displacement pump to function as will be explained below. The structure 405 is desirably a valve formed from polymeric or xenograft tissues, such as porcine aortic valves, although the present invention is not so limited. Details of various aspects of tissue valves and connections to conduits are shown and described in U.S. Pat. Nos. 5,599,173, 5,810,708 and 6,102,845 the disclosures of which are expressly incorporated herein by reference.

Valve 303 is a tilting-disk type of valve, where a disk 304 can tilt between an upwards position, as shown in the sectional view of FIGS. 4 and 5B to allow flow upwards through valve 303, and a horizontal position (not shown) to stop the flow through transfer portion 310. It is preferred that, when valve 303 is open, transfer portion 301 provides for the smooth flow of blood from chamber 220a to chamber 220b. As described subsequently, inlet and outlet conduits 24, 26 extend generally tangentially from the sacs 221, resulting in circulating flow in each sac about the central axis C in a plane parallel to midplane MP of the actuator plate 210. To accommodate the flow between sacs, it is preferred that transfer port 301 is angled by an angle θ with respect to the midplane M, as indicated in FIG. 5B. As an alternative embodiment, a bileaflet mechanical valve could be used in place of the single leaflet valve 303 described above. Another alternative embodiment armature 210' is shown in FIG. 6B as having two transfer ports 301 to facilitate flow between chambers 220.

Alternatively, a tissue valve could be used for valve 303. Since valve 303 is interior to pump 200, the use of a tissue valve would require that the pump be filled with a preservative, such as glutaraldehyde.

As another alternative embodiment, one or more conduits 32 and outlet portion 203 may be integrally formed of a suitable polymer, for example, with the valves also being formed therein of the same or a different material. Since valve structure 303 is internal to pump 200, it is more difficult to provide xenograph valves at the time of transplant, and so polymeric valves are preferable for the internal valve.

Figure 18:
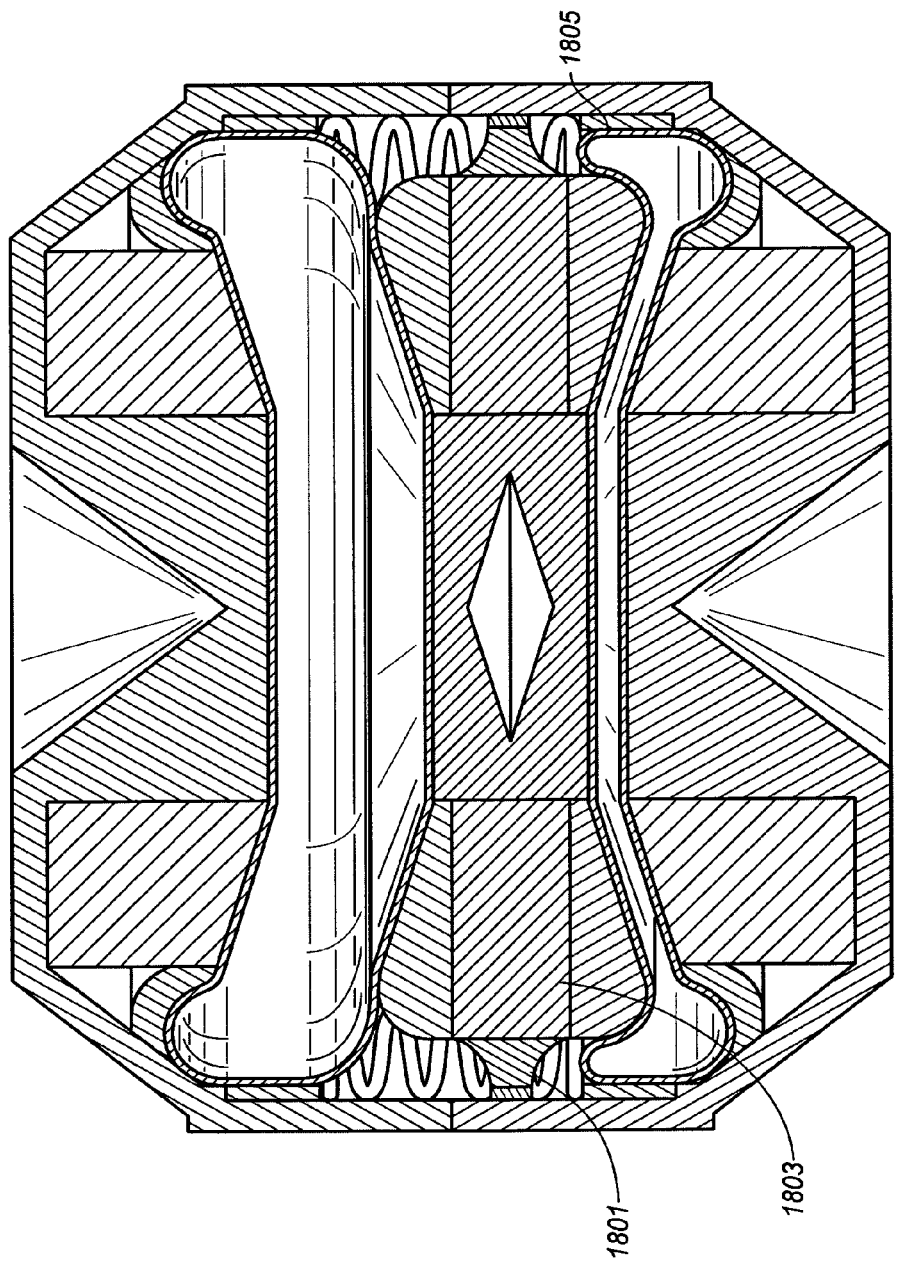
FIG. 18 is a sectional view of an alternative pump embodiment having a shoe adjacent to the magnets.

In another alternative embodiment illustrated in FIG. 18, a shoe 1801 is provided at the periphery of the magnets 1803. Shoe 1801 provides the electromagnetic advantages noted in the '601 patent. A further advantage of the shoe is that it permits part of the flexing region of the sacs 1805 to be incorporated within the thickness of the armature, against shoe 1801 and so reduces the overall thickness of the pump.

Spring Suspension

Pump 28 of the present invention also includes a suspension to stabilize the motion of actuator plate 210 within the pump, such that actuator plate remains in an orientation generally parallel to the pair of sacs 221, and such that it works in cooperation with the electromagnetic drive, as described below. The positions and spring constants of springs 231 are preferably selected such that the forces on actuator plate 210 results in a net righting force on the actuator plate that permits it to move back and forth within the frame without tilting, that is along and generally perpendicular to central axis C, as shown in FIG. 4.

While some of the features noted in the previous paragraph have similarities to the drive disclosed in the '601 patent, the spring suspension system has several features not found in the '601 patent. In particular, while the pump of the '601 patent uses springs in conjunction to an electromagnetic drive that is similar to that of the inventive pump, the springs of the '601 patent cooperated with the electromagnetic drive system of the '601 patent to balance the forces about midplane M and thus neutrally suspends the armature between the chambers. In contrast, springs 231 of the present invention provide a "spring force" on the actuator plate that is towards the high-pressure pump chamber. The bias force is useful in that it allows the springs to store and deliver energy from the electromagnetic drive system to provide better utilization of the pump components, and to reduce the pump size and consumption of electricity.

Springs 231 are preferably configured to be linear with a total spring constant k, and having a position offset that, in conjunction with the axial force produced by the permanent magnets, produces a bias force towards chamber 220b irrespective of the placement of actuator plate 210. Specifically, the springs are positioned so that their net force on actuator plate 210 is zero at a distance h from midplane M, resulting in a spring force $F_S$ of:

$$F_S = k(h-x). \tag{1}$$

Springs 231 are in compression throughout the travel of actuator plate 210, thus reducing fatigue in the spring from the reciprocating load, and simplifies spring retention. Shims, adjusting screws, and/or selected spring sizes may alternatively be used to level the actuator plate 210 during pump fabrication, and, as described below, to correctly balance the magnet force, and to set the proper eject assist pressure. In addition, each pair of spring produces the same force at the same distance from center line C.

One embodiment of the suspension is illustrated for pump 200. Forces on actuator plate 210 within frame 209 are provided by four pairs of springs 231 that are disposed at the same approximate radial position about the periphery of the actuator plate at tabs 211. Each pair of springs 231 is positioned with one on each side of tab 211 of actuator plate 210, and between surface 235 of frame 209. The clearances between surfaces 235 and the adjacent tabs 211 are all the same. The spring forces of springs 231 are selected so that, with actuator plate 210 perpendicular to axis C, each of the pairs of springs 231 each exert the same force on symmetrically disposed tabs 211, and that the total force of all of springs 231 with the actuator plate so oriented is parallel to axis C. Any motion actuator plate 210 that is not perpendicular will result in displaced spring forces that will exert a moment on the actuator plate and will tend to force it back to a perpendicular orientation.

Exemplary springs 231 are shown as helical compression springs, any spring configuration that similarly resists displacement of the armature 210 may be used, for example, leaf springs or one large spring on the side of one of the pairs of chambers 220 such as a large diameter coil spring. It is preferred that each of the exemplary springs 231 are always in compression to reduce fatigue on the springs, simplify retention, and avoid separation and subsequent contact of springs 231, frame 209, and armature 210 during armature motion.

VAD Operation

As mentioned above, the drive system (a preferred embodiment of which is described below) displaces the armature, or actuator plate, 210 to alternately compress each variable-volume chamber 221. FIGS. 7A to 7F present schematic views of one configuration of pumping chambers of the present invention. In accordance with the series flow blood pump 28 exemplified in FIGS. 2–6A, blood from the ventricle is initially pumped to the first chamber 220a through inlet conduit 24. The drive system is first activated in a 'pump stroke' to displace armature 210 to the right as shown by the arrow in FIG. 7A, thereby ejecting blood received within second chamber 220b through valve 205, into outlet conduit 26, and through outlet segment 32 for delivery to the aorta. During the pump stroke of armature 210, valve 303 prevents blood from flowing through transfer portion 301. In addition, pump 200 actively fills during the power stroke since the first chamber 220a is expanding, thereby drawing oxygenated blood through the inlet conduit 24 from the left ventricle LV into the left chamber as shown in FIG. 7B. During the power stroke, blood is thus flowing though both of conduits 24 and 26, as well as flowing into chamber 220a and out of chamber 220b. At the end of the pump stroke as shown in FIG. 7C with the armature 210 positioned to the right, the first chamber 220a is filled with oxygenated blood from the left ventricle, and the second chamber 220b is compressed to a minimum volume. At the end of the power stroke, valve 205 will close, and pumping ceases. As described below, there are some inertial effects of the flowing blood that may result in continued flow for a brief period of time after the end of the power stroke (this is referred to as dynamic ejection, as described below).

Preferably soon after the end of the power stroke, the drive system is activated to execute a 'transfer stroke' to move the armature 210 to the left as shown by the arrows in FIGS. 7D and 7E, thereby drawing blood from the first chamber 220a into the second chamber 220b via the transfer portion 301. The outlet valve 205 prevents blood in the aorta or the outlet conduit 26 from being drawn back into the second chamber 220b. In addition to left ventricular pressure, the low pressure within the second chamber 220b caused by the expansion of the chamber ensures that blood within the first chamber 220a enters the second chamber 220b and is not ejected back into the inlet conduit 24. Thus during the transfer stroke, there is no net flow through pump 200. At the end of the transfer stroke as shown in FIG. 7F with the armature 210 positioned to the left, the second chamber 220b is filled with oxygenated blood from the left ventricle, and the first chamber 220a is compressed to a minimum volume. The pump stroke illustrated in FIGS. 7A–7C and the transfer stroke illustrated in FIGS. 7D–7F may be repeated in accordance with the exemplary methodology of the invention described below.

In general, different amounts of power are required by armature 210 to execute the transfer stroke and the pump stroke. Specifically, the transfer stroke transfers blood from chamber 220a to chamber 220b with no net flow through pump 200, while the pump stroke consumes energy in raising the pressure in chamber 220b and pumping fluid from the pump.

Preferred Electromagnetic Drive System

Figure 8A:
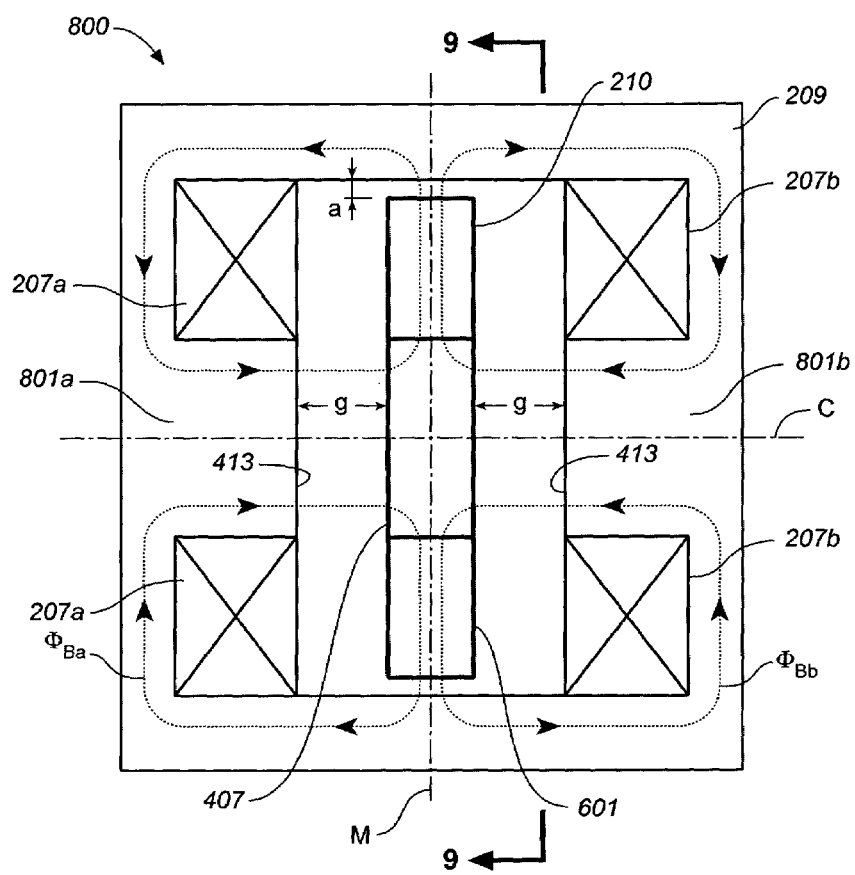
FIG. 8A is a schematic view of an exemplary drive structure of the invention, illustrating a magnetic flux path generated by a magnet on an armature, shown in an equilibrium position.
Figure 8B:
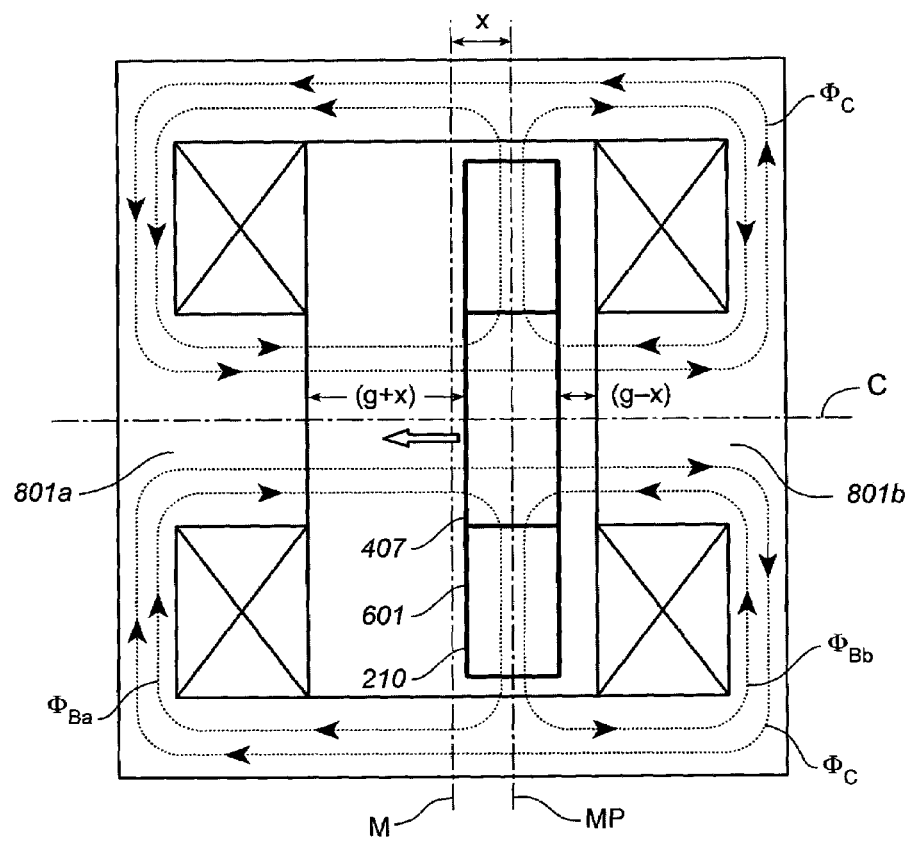
FIG. 8B is a view similar to that of FIG. 8A, showing the armature displaced to the right and being driven to the left and illustrating the magnetic flux paths including a coil flux path generated by a fixed electromagnetic coil.
Figure 8C:
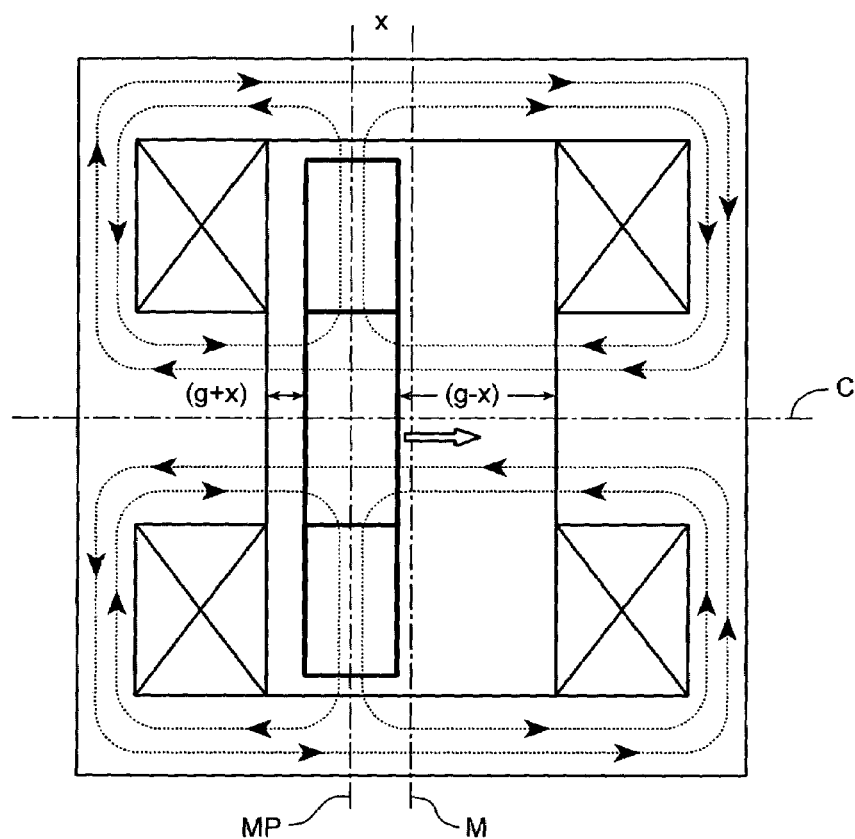
FIG. 8C is a view similar to that of FIG. 8A, showing the armature displaced to the left and being driven to the right and illustrating the magnetic flux paths including a coil flux path generated by a fixed electromagnetic coil.
Figure 9:
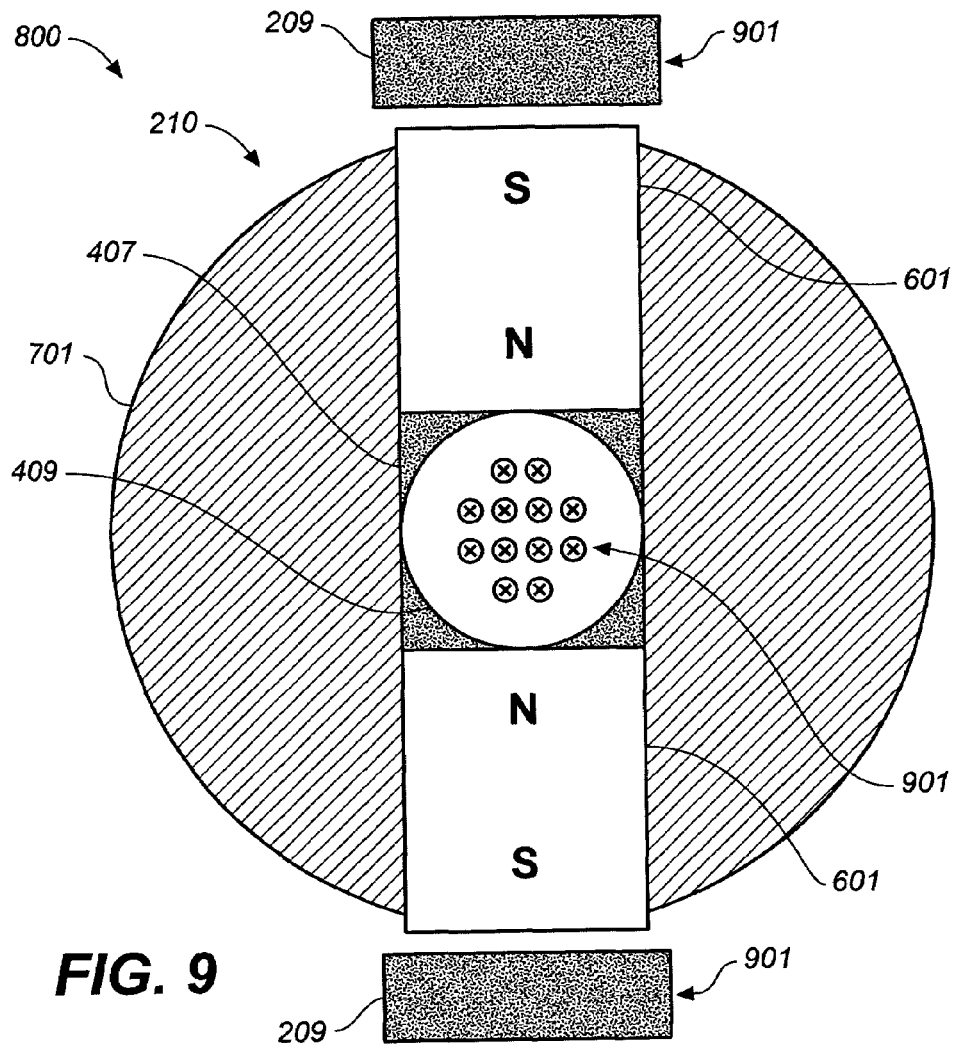
FIG. 9 is a schematic view of an exemplary drive structure of the invention, illustrating the magnetic flux perpendicular to the center axis and through the armature.

The preferred electromagnetic drive system of the invention will now be described with reference to FIGS. 4, and 7–9. In particular, FIG. 8A is a schematic view of an exemplary drive structure of the invention, illustrating a magnetic flux path generated by a magnet on an armature (shown in an equilibrium position), FIG. 8B is a view similar to that of FIG. 8A, showing the armature displaced to the right and being driven to the left and illustrating the magnetic flux path including a coil flux path generated by a fixed electromagnetic coil, FIG. 8C is a view similar to that of FIG. 8A, showing the armature displaced to the left and being driven to the right and illustrating the magnetic flux path including a coil flux path generated by a fixed electromagnetic coil, and FIG. 9 is a schematic view of an exemplary drive structure of the invention, illustrating the magnetic flux perpendicular to the center axis and through the armature.

For the purposes of this description, the drive system includes an electromagnetic structure 800 having center axis C and midplane M. With reference to FIGS. 4, 8, and 9, electromagnetic structure 800 includes frame 209 in which is mounted the pair of electrically-conductive coils 207, including a first coil 207a and a second coil 207b, and armature 210. As shown in FIGS. 4 and 8, the coils 207 are disposed in a spaced relationship within the frame 209 on opposite axial sides of the armature 210. Coils 207 may be configured as annular rings having trapezoidal, rectangular or other shapes to best utilize the space within pump 200 for producing a field as described herein with a minimum weight. The coils 207a and 207b are powered with approximately equal values of amp-turns (NI) to generate a magnetic flux $\Phi_c$ defining a pair of poles 801, including a first 801a and a second pole 801b, as shown in FIGS. 8B and 8C. Poles 801 are generally contained within frame 209 and present surfaces 413 to the interior of the frame. The polarity of the electric circuit through the coils 207 determines the magnetic flux direction as shown in FIGS. 8B and 8C and, thus, the physical influence on the armature 210.

The armature 210 is disposed within the frame 209 between the poles 801 and the magnets 601 positioned between the coils 207. When the armature 210 is centered between the poles 801 at the midplane M, a gap g is defined on either side of the armature, as shown in FIG. 8A. In addition, an annular gap a having a substantially constant radial dimension is defined between the radially outermost surface of the armature 210 and an inner surface of the frame 209.

With reference to FIGS. 4 and 8, each of the poles 801 defines an inwardly facing surface 413, generally within the annular coils 207, disposed normal to the central axis C and facing the armature 210. The frame 209 includes a pair of centrally-located, outwardly-facing conical cavities 521a and 521b so that the poles 801 comprise annular regions 415 that transition along the cylindrical cavities 521 to the area of the inwardly facing surfaces 413. In this manner, the overall mass of the device is reduced which helps facilitate patient acceptability and comfort. Alternative embodiments (not shown) include cavities 521 that are cylindrical or that have other symmetric shapes about center line C.

As is best seen in the sectional view of FIGS. 4–6A armature 210 is a generally planar structure that includes a central core 407 of a magnetically permeable material and two symmetrically placed magnets shown as a pair of magnets 601 about the central core. Armature 201 also includes a non-magnetic material 701 that fills out the remainder of the actuator plate structure, specifically the pair of spaced apart, actuator surfaces 401 and the four tabs 211 about the periphery of the armature. The pair of magnets 601 and magnetically permeable portion 407 are situated so as to provide a magnetic flux shown as paths $\Phi_{Ba}$ and $\Phi_{Bb}$. As is seen in the top view of FIG. 9, the return path 901 of magnetic flux path $\Phi_{Ba}$, $\Phi_{Bb}$ is through frame 209 and near magnets 601. The springs 231 may also provide a return path for the magnetic flux.

The magnetic flux path $\Phi_{Ba}$, $\Phi_{Bb}$ tends to create an instability of armature 210 in a central position between the two variable-volume chambers 220, due to the attraction of magnets 601 to frame 209. The instability tends to bias armature 210 toward one or the other variable-volume chamber 220 upon a slight displacement in that direction. This bias produces a force on armature 210, in the absence of any energization of coils 207 that varies with increasing displacement from midplane M that is referred to herein as the "magnetic force."

Also shown in FIGS. 4 and 6A, armature 210 has a diamond-shaped hollow center 409 in core 407, which reduces the weight of the pump 28. More to the point, the hollow center 409 reduces the mass of armature 210. In addition, the reduced mass also results in a reduced power (and battery size) needed to displace it, and in turn reduces the size the electromagnetic drive components. The entire device can thus be reduced in size to further facilitate successful implantation.

Figure 12:
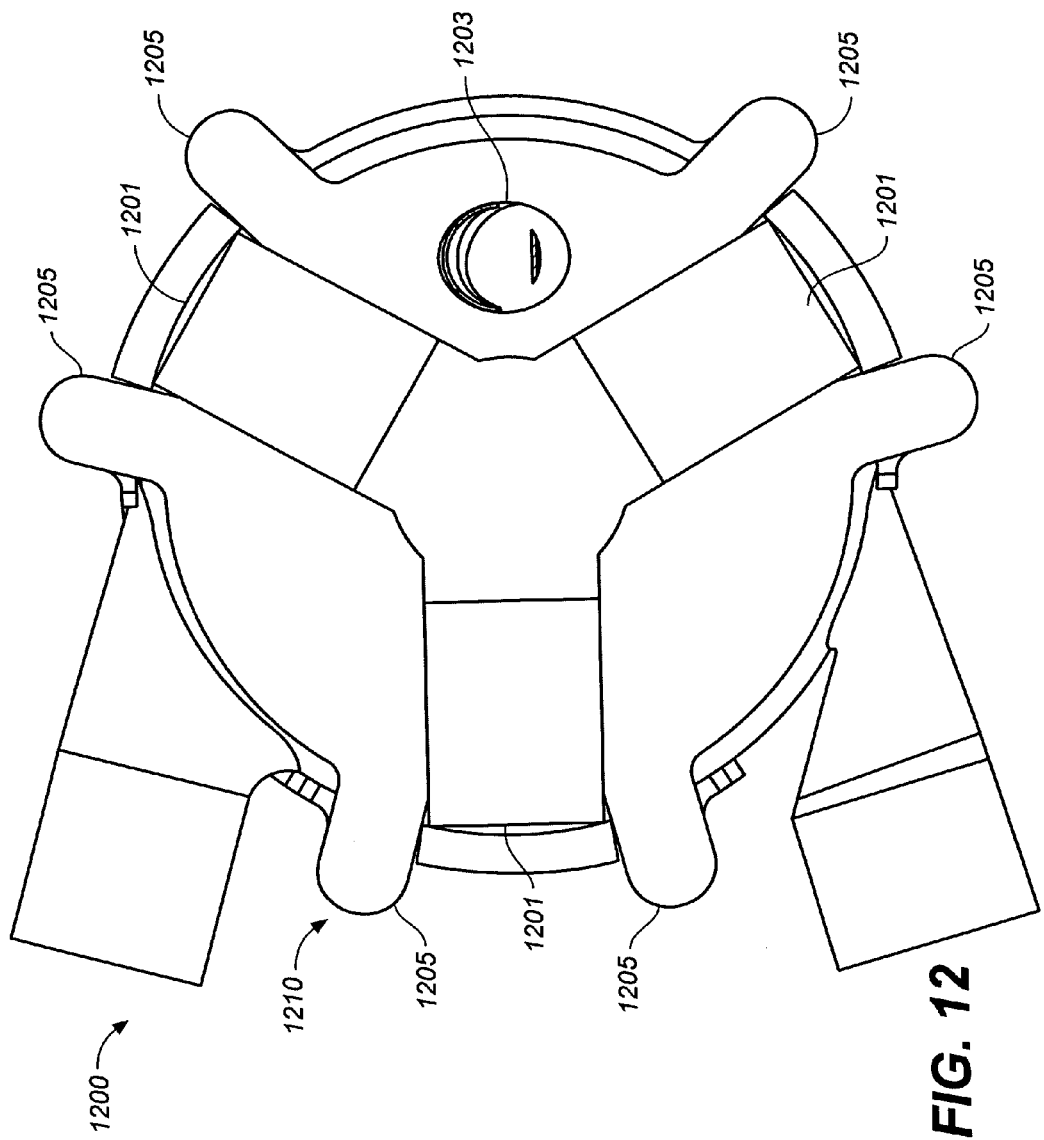
FIG. 12 shows an alternative armature embodiment having three magnets.

The use of a pair of magnets 601 in armature 210 is an inexpensive alternative to symmetrical magnets, such as those of the '601 patent, for example. In addition, magnets 601 take up less space in armature 210, allowing for other uses for the armature, such as by placing transfer portion 301 through the armature. The present invention includes electromagnetic structures having more than two magnets, such as three or more magnets, as well as other spring arrangements for stabilizing armature movement. It is preferred that the magnets be placed with like poles towards center line C, and that they be symmetrically placed about the center line to keep the armature balanced. FIG. 12 shows an alternative embodiment of a pump 1200 having an armature 1200 with three magnets 1201, surfaces 1205 for receiving springs on either side of each magnet, and a transfer port 1203.

Electromagnetic Drive System

Radially polarized magnets 601 generate bias flux $\Phi_B$ that follows a closed magnetic circuit including the frame 209, a respective one of the poles 801, a respective one of the gaps g, and the armature 210. Bias flux $\Phi_B$ is shown as $\Phi_{Ba}$ for the flux that goes about coil 207a and as $\Phi_{Bb}$ for the flux that goes about coil 207b. Advantageously, electromagnetic flux $\Phi_C$ generated by the coils 207 does not travel a path through the magnets 207, but instead traverses around the outside of the frame 209 and through the poles 801, gap g, and armature 210; accordingly, the bias flux $\Phi_B$ remains substantially constant and predictable. As the bias flux $\Phi_B$ is substantially constant, the magnet 601 is not subject to depolarization, which is discussed in more detail below.

The armature 210 moves either towards pole 801b as shown in FIG. 8B or towards pole 801a as shown in FIG. 8C by a distance indicated as x. With particular reference to FIG. 8B, when electrically activated, the coils 207 generate coil flux $\Phi_C$ which follows a path including the frame 209, one of the poles 801a or 801b, one of the gaps (either [g+x] or [g−x]), the armature 210, the other gap, the other pole, and the frame.

Details of electromagnetic structure 800 are presented in the '601 patent. In particular, it is preferred that the electromagnetic structure 800 is a linear magnetic structure. Following the presentation of the '601 patent, the electromagnetic structure 800 is configured so that:

(a) the coil flux $\Phi_C$ follows a substantially closed path to make efficient use of the magnets 601;

(b) the total bias flux $\Phi_B$ is substantially constant to eliminate depolarization of the magnets 601, which generates the bias flux;

(c) a relatively low magnetic field intensity (H) over a relatively large area A of the poles 801 significantly reduces the need for high-precision components; and (d) energy conversion is linear to simplify optimization and control.

In particular, electromagnetic structure 800 is configured so that the maximum values of the fluxes $\Phi_{Ba}$ and $\Phi_{Bb}$ traversing between the armature 210 and the poles 801 of FIG. 8B (and the connected parts of electromagnetic structure 800) are below the magnetic saturation level of the armature 210 and poles 801; accordingly, the magnetostatic equivalent circuit of electromagnetic structure 800 is linear. Also, electromagnetic structure 800 is preferentially configured so that fringing magnetic fields located around the poles 801 and the annular gap are insignificant. One way for the resulting magnetostatic equivalent circuit to be approximately linear is for the poles 801 to preferably have a relatively large pole area $A_{pole}$. Accordingly, the magnetic flux density (B) is preferably on the order of 0.5 tesla (T) for an exemplary blood pump embodiment. A magnetic flux density of this magnitude is significantly less than the magnetic flux density saturation ($B_{SAT}$) of core material used in the armature 210 and the poles 801. Therefore, exemplary armature 210 may have a hollow center 409 (as shown in FIGS. 6A and 6B) to reduce the weight of the overall electromagnetic structure 800.

As the electromagnetic system is linear, the fields can be treated separately and superimposed. As presented in the '601 patent, accordingly, the bias fluxes $\Phi_{Ba}$ and $\Phi_{Bb}$ and the coil flux $\Phi_C$ may be calculated separately and, with no current through coils 207 (I=0) the total energy and force on armature 210 along center axis C is:

$$W_b = \Phi_B^2(g^2-x^2)/4 \ \mu_o g A_{pole}; \text{ and}$$

$$F_b = -\partial W_b/\partial x = \Phi_B^2 x/2 \ \mu_o g A_{pole}, \quad (2)$$

where $\mu_o$ is the permeability of free space ($4\pi 10^{-7}$ in SI units). Accordingly, as the armature 210 moves towards pole 801a, the bias flux $\Phi_B$ shifts from left to right, with the total flux $\Phi_B$ remaining constant. As energy W and force F vary with $\Phi_B^2$, the shift in force $F_b$ is marked. This phenomenon is illustrated in FIG. 8B. The shift in the force $F_b$ constitutes a negative spring that can be used to balance the suspension system provided by springs 213, which will be discussed in detail below. As shown in the equation for $W_b$ and $F_b$, the energy and force are both independent of coil current.

Magnets 601 are preferably made from a material having a high energy density and a low marginal permeability, for example, rare earth material such as samarium cobalt (SmCo) or neodymium iron (NdFe). Accordingly, the magnets 601 as described above are a source of flux. Therefore, the bias flux $\Phi_B$ is constant in the magnets 601, and all of the flux $\Phi_C$ generated by the coils 207 traverses the loop shown by the lines in FIG. 8B, including the frame 209, the pole 801a, the gap (g+x), the armature 210, the gap (g−x), the pole 801b, and the frame 209.

The force contributed by the coil current I from a coil having N turns is calculated from the total energies in the left and right gaps (holding the bias fluxes $\Phi_{Ba}$ and $\Phi_{Bb}$ constant):

$$F_C = -NI\Phi_B/2g, \quad (3)$$

The coil force $F_C$ is independent of displacement x and area A and is linear in flux $\Phi_B$. Accordingly, the following total electromagnetic force $F_{EM}$ equation results from the force $F_B$ and the coil force $F_C$ respectively represented by Equations 2 and 3:

$$F_{EM} = F_b + F_C = \Phi_B^2 x/2 \, \mu_o g A - N I \Phi_B/2g \quad (4)$$

Equation 4 enables wide design latitude through varying the flux. $\Phi_B$ and the area A of the poles 801 as the area $A_{pole}$ does not contribute to the coil force $F_C$. For example, it is desirable for the value of the flux $\Phi_B$ to be large as flux directly determines the coil force $F_C$ generated by a given coil current I. For a given coil geometry, force $F_C$ is proportional to the product of number of turns N and coil current I (that is, $F_C \propto NI$), and power dissipation $P_{Diss}$ is as follows:

$$P_{Diss} = I^2 R \propto (NI)^2 \quad (5)$$

Accordingly, efficiency may be improved by using a high flux $\Phi_B$ and a modest NI. To prevent the large flux $\Phi_B$ from developing too much force $F_b$, which is balanced by springs 231 as described below, the poles 801 preferably have a relatively large area $A_{pole}$. A large pole area $A_{pole}$, in turn, implies a low value of magnetic flux density B; accordingly, the effect of fringing fields is minimized or substantially eliminated.

Electromagnetic Drive System and Energy Storage

The approximate forces acting on actuator plate 210, and the resulting operation of the combined drive and energy storage mechanisms, will now be illustrated for ideal magnets and spring forces. The total drive and energy storage force, $F_{total}$, acting on actuator plate 210 is given by the sum of the electromagnetic force of Equation 4 and the springs force of Equation 1 as:

$$F_{total} = F_b + F_S + F_C \quad (6)$$

The first two terms of Equation 6 is a net bias force $F_{bias}$ that is independent of coil current I:

$$F_{bias} = F_b + F_S = [\Phi_B^2 x/2 \, \mu_o g A_{pole}] + [k(h-x)] \quad (7)$$

If the spring constant k and electromagnetic drive constants $\Phi_B'$ g, and $A_{pole}$ are selected such that:

$$k = \Phi_B^2/2 \, \mu_o g A_{pole}, \quad (8)$$

then the net bias force $F_{bias}$ is:

$$F_{bias} = kh = h\Phi_B^2/2 \, \mu_o g A_{pole}, \quad (9)$$

and is thus also independent of the position of actuator plate 210. The total force $F_{total}$ is:

$$F_{total} = F_{bias} + F_C = h\Phi_B^2/2\mu_o g A_{pole} - NI \, \Phi_B/2g, \quad (10)$$

The total force is thus independent of the position of actuator plate 210, and is the sum of a net bias force that is independent of coil current I and a coil force that depends linearly on the coil current I.

Figure 10:
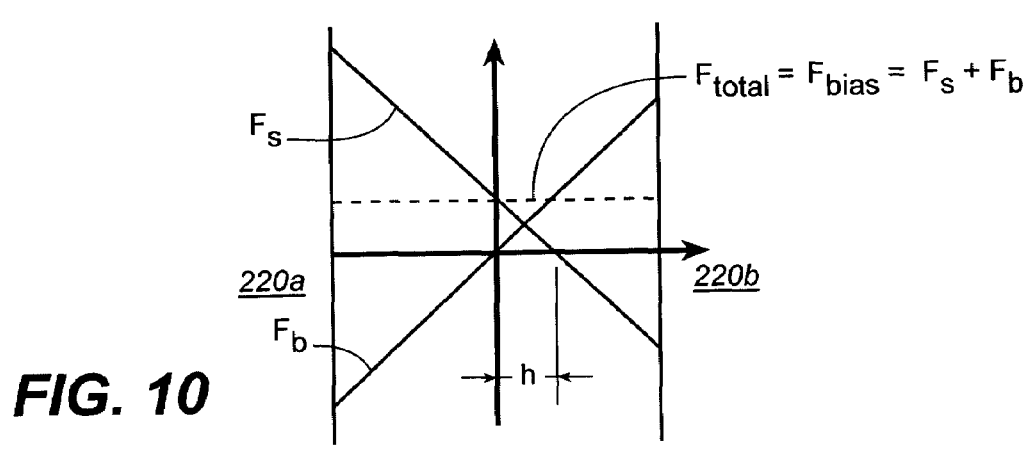
FIG. 10 is a graph showing the bias forces of the drive structure superimposed along a position axis.

The sum of the bias forces is shown graphically in FIG. 10 as a graph of the bias forces. The spring force $F_S$ resulting from the force of suspension springs 231 on the actuator plate 210, and the magnetic force, $F_b$, resulting from of the attraction of armature 407 towards surfaces (stator pole) 413 are selected through Equation 8 to result in position independent bias force. Specifically, the springs 231 and the structure 800 are selected such that the sum of the spring force opposes the magnetic force and such that the sum of the spring force and magnetic force is a force towards chamber 220b that is a constant bias force approximately independent of the position of armature 210 in frame 209.

It is preferred that the bias force produces a pressure (given by the total force $F_{total}$ divided by the actuator plate area, $A_{AP}$) in chamber 220b that allow actuator plate 201 to remain between actuator stops 233 under the action of the aortic and ventricular pressures, and that does not permit either of one-way valves 205 or 303 to open between the end of one systole and the beginning of the next. In preferred embodiments, pressure $F_{bias}/A_{AP}$ is typically 40 to 50 torr for left ventricular assist, and 20 to 40 torr for right ventricular assist, with the remainder of the pressure delivered by the force $F_C$.

In general, the ability to control the pump pressure and timing through the coil current allows for many advantages. The pump can be run at a rate that is on the order of the physiological time of a beating heart, reducing the peak pressure in comparison with other types of drives, and thus improving the lifetime of moving parts, such as the one-way valves. The controllability of the pressure according to the applied coil current also allows the pressure to be tailored during the pump stroke, allowing for example, an increased pump rate near the end of the pump stroke.

In one embodiment, pumping occurs by imposing a coil current that alternates direction between strokes ($I_{pump} = -I_{transfer}$). In addition, the times over which the power and transfer strokes occur are approximately the same such that the total power delivered to coils 207 during the transfer stroke and the power stroke is the same, optimizing the use of electrical and electromagnetic components. During the transfer stroke, electromagnetic power is transferred to armature 210 to transfer blood from chamber 210b to chamber 210a, and to compress and thus store energy in springs 231. During the power stroke, electromagnetic power is transferred to armature 210 and the expanding springs 231 release stored energy to augment the electromagnetic power. The springs thus serve to store energy and effectively load level the electromagnetic drive energy, and the electromagnetic drive operates at one-half the average pumping power, better utilizing power and pump components.

During the pump stroke, valve 303 is closed, and the motion of actuator plate 210 draws blood from inlet conduit 24 into chamber 220a and pushes blood from chamber 220b into outlet conduit 26. Immediately at the end of the pump stroke, actuator plate 210 stops. Because of the momentum of blood flow on either side of the actuator plate, there is a tendency for valve 303 to momentarily open at the end of the pump stroke, allowing for the "dynamic ejection" of blood after the end of the pump stroke. As a result of valve 303 opening and the momentum of blood on either side of actuator plate 210, the volume of blood delivered for each pump stroke can be larger than the volume of chamber 220b. Dynamic ejection thus allows for the use of a pump having a volume that is less than the volume of blood to be pumped on each stroke.

The magnitude of dynamic ejection is proportional to the pressure across valve 303 at the end of the pump stroke. During the power stroke, a force $F_{pump}=(h\Phi_B^2/2\ \mu_o\ gA_{pole}+NI\Phi_B/2)$ is generated by the drive and recovery of energy from the springs to give a pump pressure, $P_{pump}$ of:

$$P_{pump}=F_{pump}/A_{AP}=(h\Phi_B^2/2\ \mu_o gA_{pole}+NI\Phi_B/2)/A_{AP}. \quad (11)$$

The amount of dissipation in the coils is proportional to the square of the coil current, and thus the energy efficiency of dynamic ejection is limited by dissipation.

Pump 200 will thus develop a positive pressure across the actuator plate 210, and open the transfer valve 303, allowing continuing through flow in excess of the static capacity of the pump. This does not, however, imply two opening and closing cycles for this valve each stroke, because, as discussed below, the control algorithm preferably begins the transfer stroke immediately at the end of the pump stroke. The dynamic flow then decelerates as its kinetic energy is extracted to continue moving blood against the afterload.

In another embodiment, the coil currents and stroke times for pumping and transfer are not a priori selected to have the same magnitude, but are selected to provide a high overall system efficiency. By adjusting the currents and stroke times to eject and transfer blood with the time between sequential pump cycles, the total energy dissipation can be reduced with a resulting increase in system efficiency. In one embodiment, the pumping and inter-pump transfer flow rates are selected to minimize dissipation in the nominal case where extra time is available between strokes. One particular embodiment provides a pumping flow rate of 300–400 ml/sec, while the minimum flow rate needed to keep up with the cardiac cycle and allow for the controlling "wait" interval between the transfer and pump strokes is in the range of the 250–300 ml/sec.

Figure 11:
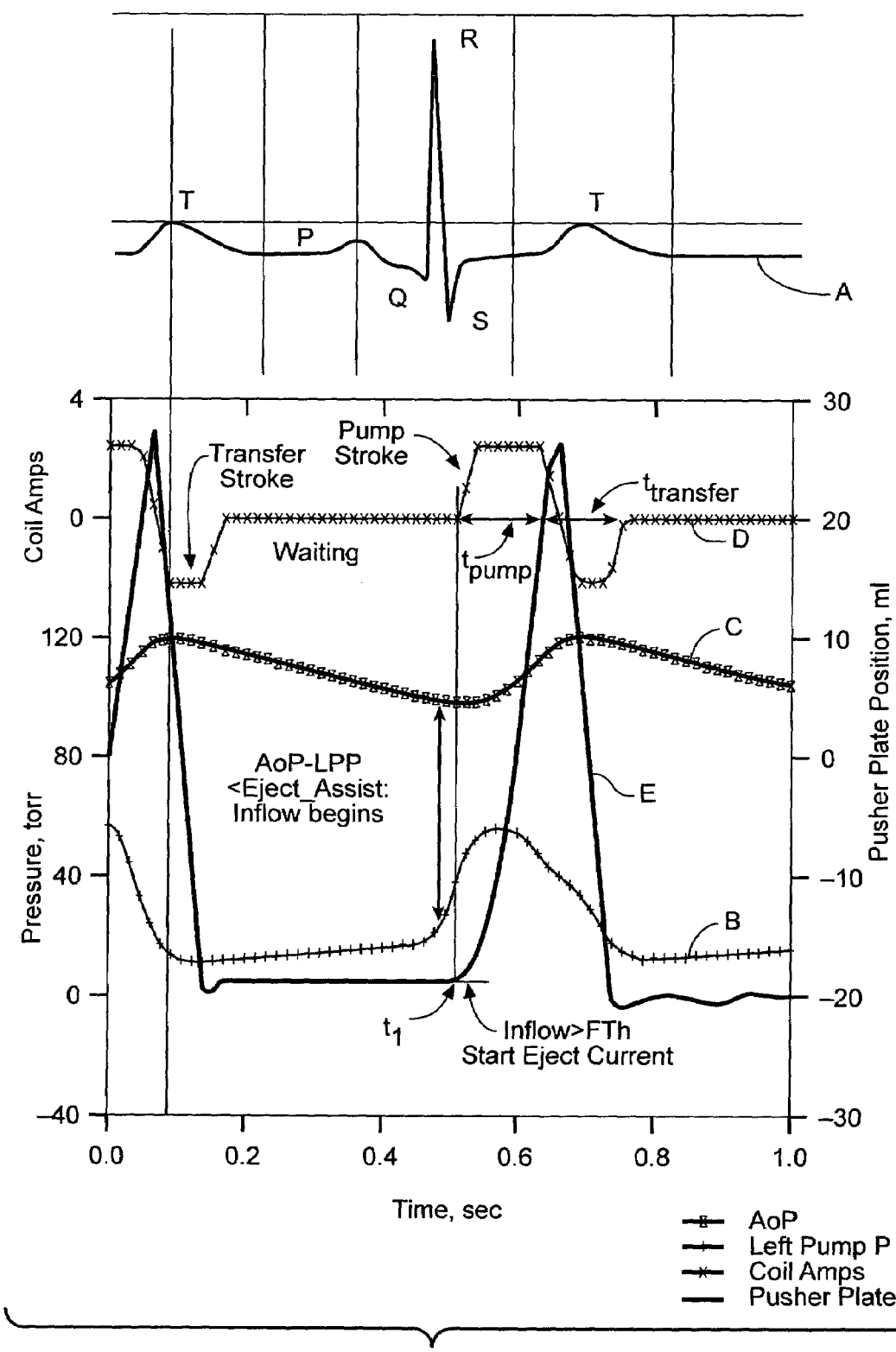
FIG. 11 illustrates the operation of the inventive pump for assisting the pumping of the ventricle, where trace 11A is an exemplary electrocardiogram (ECG) record of the changing potentials of the electrical field imparted by the heart, trace 11B is the left ventricular pressure, trace 11C is the aortic pressure, trace 11D is the power to the pump coils, and trace 11E is the position of the actuator plate.

Ventricular Assist System—Control and Coordination with Heart under Normal Conditions Referencing FIG. 11 and taking the foregoing into consideration, it is advantageous from an energy point of view to accept and pump blood ejected by the assisted ventricle during systole (i.e., ventricular contraction) as rapidly as is consistent with fluid flow considerations, and to stop pumping during diastole (i.e., ventricular dilation).

As shown in FIG. 11, trace 11A is an exemplary electrocardiogram (ECG) record of the changing potentials of the electrical field imparted by the heart, trace 11B is the left ventricular pressure, and trace 11C is the aortic pressure. To briefly explain the cycle of systole and diastole, the ECG signal shown in FIG. 11 illustrates a series of points representing various muscle contractions within the heart. Generally, blood is received in the left ventricle and it fills during the T-Q period. Then, during the period Q-T, the left ventricle contracts and expels blood into the aorta (systole). Accordingly, the pressure diagram in FIG. 11 shows the left ventricular pressure rapidly increasing during the spike indicated at R on the ECG signal. For the purposes of this description, ventricular systole may be considered as occurring between the R and T points on the ECG wave. The pressure in the aorta is a maximum at the end of the R-T period and generally varies with a smaller pressure variation and more smoothly than the ventricular pressure.

Also shown in FIG. 11 is trace 11D showing the power to the pump coils, and trace 11E showing the position of the actuator plate 210. When the heart enters systole (e.g., at the beginning of the QRS complex of the ECG), the pressure within the LV begins to rise. The pressure in chamber 220a, which is in fluid communication with the LV through conduit 24, will also begin to rise as indicated by trace 11B. This slight increase in pressure, augmented by springs 231 will cause a slight movement of actuator plate 210 towards chamber 220b. A signal indicative of this movement, sensed as discussed subsequently, is assumed to indicate the beginning of systole.

According to a preferred control strategy, controller 40 receives the indication of movement of actuator plate 210 at a time $t_1$ and triggers pump 220 to assist the ventricle by activating coils 207 to a current I for a time $t_{pump}$ as indicated in trace 11D, and thus move the armature 210 towards chamber 220b to pump blood into the aorta AO, and to accept blood from the LV into chamber 220a. If the LV is nearly empty, the pressure rise in chamber 220a will not be sufficient to move actuator plate 210, and controller 40 will not initiate the pump stroke. Upon completion of the pump stroke, controller 40 causes the current flow through coils 207 to be reversed, initiating the transfer stroke. At the end of the transfer stroke, the current to the coils is reduced to zero as the pump waits for the next increase of systolic pressure and a repeat of the pump stroke.

If the patient's physiologic state is such that the LV stroke volume is equal to the stroke volume of the VAD, then the phasing between the heart and the VAD will be as illustrated in FIG. 11 on every beat, and the pump rate will be equal to the heart rate. In the general case, however, the LV stroke volume may be smaller or larger than the VAD stroke volume. If the LV stroke volume is smaller than the VAD stroke volume, the volume absorbed into the transfer chamber during each pumping stroke will be greater than the LV stroke volume. Average LV volume will decrease, resulting in a general decrease in LV pressure. If the LV is nearly empty, the pressure rise in chamber 220a during the wait period will not be sufficient to move actuator plate 210, and controller 40 will not initiate the pump stroke. The average pump rate will thereby be lower than the heart rate, such that the pump output (VAD stroke volume times average pump rate) equals the cardiac output (LV stroke volume time heart rate).

Conversely, if the LV stroke volume is larger than the VAD stroke volume, the VAD can not absorb the entire LV stroke volume into the transfer chamber during the pumping stroke, and the subsequent transfer stroke will begin before the end of LV systole. If the end of the transfer stroke is reached while the pressure in the LV is still high, a second pump stroke/transfer stroke will be initiated without waiting for the start of the next LV systole. The average pump rate will thereby be higher than the heart rate, such that the pump output (VAD stroke volume times average pump rate) equals the cardiac output (LV stroke volume time heart rate). Thus pump 28 is said herein to nominally pulse once per heart beat, but it is understood that the pump is being triggered from variations in the blood pressure, and thus the pump may execute a pump/transfer stroke sequence at more or less than the cardiac cycle.

Above the threshold pressure needed to overcome the aortic pressure, the outflow rate will be determined by pressure differential across actuator plate 210, and therefore also by coil current I. These factors lead to choice of an optimum ejection rate by determining I, $t_{pump}$, and $t_{transfer}$ that requires the lowest stroke energy. It is advantageous, both energetically and to minimize blood shear rate, to perform most of each stroke near this optimum rate. Thus outflow will typically still be near its mean rate when the pump reaches the end of its ejection stroke.

During the wait between the end of a transfer stroke and the beginning of the next ejection stroke, there is no coil current (I=0), and thus no electrical dissipation. It is preferred that during this waiting state that actuator plate 210 is resting without tabs 211 contacting actuator stops 233. The blood in chamber 220a is thus pressurized by the action of the net bias force with a pressure of $F_{bias}/A$. During diastole, the pressure $F_{bias}/A$ is not large enough to open valve 205, and thus actuator plate will remain with chamber 220a at or near minimum volume. When the ventricle pressure rises, the pressure in chamber 220b will rise accordingly until valve 205 opens. This will ensure that an increase in the pressure of the LV will result in movement in actuator plate 210 that can be sensed to trigger pump 200. The rising ventricle pressure is augmented by the net bias force produced by the springs, so that the pressure in chamber 220a exceeds the aortic pressure, allowing detectable motion of the actuator plate, long before ventricle pressure would be sufficient to overcome aortic pressure. Aortic root flow is possible only if LV systole persists into the transfer stroke.

Since the force and thus total pressure blood pressure generated within each chamber 220 is approximately independent of the position of the armature 210 and is dependent on the coil current, as indicated by Equation 9, the pressure is easily controllable and can be electrically adjusted. In particular, it may be desirable to periodically adjust the threshold or to periodically test the effect of modifying the threshold for improved pump performance or to alter the amount of energy exerted by the pump, and thus the amount of work required by the patient's heart H. The threshold in the device of the present invention can be adjusted electronically from pulse to pulse, if required. One method of adjusting the threshold is to apply a small current to the coils between pulses. Another method of adjusting the threshold is by changing the amount of actuator plate movement or chamber pressure required to trigger the pump. Electronic adjustment of the threshold permits programming the threshold at which the transfer stroke is initiated at the start of LV systole. Since the coil dissipation is proportional to $I^2R$ (Equation 5), and the current needed for such threshold adjustment is small relative to the driving current, the energy and efficiency cost of electrically modifying the threshold setting is modest.

Ventricular Assist System—Control and Coordination with Heart During Arrhythmias Patients with ventricular arrhythmias needing ventricular assist are normally provided with bi-ventricular support. However, there is anecdotal evidence that patients on LVADs can tolerate arrhythmias, and thus patents with ventricular arrhythmias may in the future receive LVAD support under some conditions. In particular, it is important that patents receive an adequate amount of circulatory support to reduce the potential for reduced perfusion and increased risk of thromboembolic complications (primarily due to stasis, pooling, dilation). The experience at the Cardiovascular Devices Division of the University of Ottawa Heart Institute, with animals supported on assist devices and subjected to ventricular fibrillation (VF), found that sustained periods of maximal support by the device can lead to recovery from extended periods of VF and return to sinus rhythm. In addition, long term circulatory support (weeks) in animals with refractory VF was able to maintain sufficient blood flow to eliminate the risk of perfusion deficit and thromboembolic events by utilizing active filling modes.

Currently most ventricular assist devices run in two principal modes, which can provide either passive (no suction) or active (utilizing suction) filling modes. In addition, these devices use principally use two operating rates: either a fixed rate (rate is set to a specific operating rate measured in beats per minute—BPM) or an automatic mode (rate derived from sensors determining end points i.e. position at fill, empty, etc). Both of these operating rates have drawbacks under certain physiological states. For instance, fixed rate works well in at a given level of activity. However, if the activity level of the recipient is increased the pump does not provide sufficient output to match the physiological requirements. Automatic mode, on the other hand, may not respond adequately in the case of atrial and/or ventricular arrhythmias (abnormal heart rhythms) and other physiological states such as hypovolaemia (decreased volume of circulating plasma).

Figure 17:
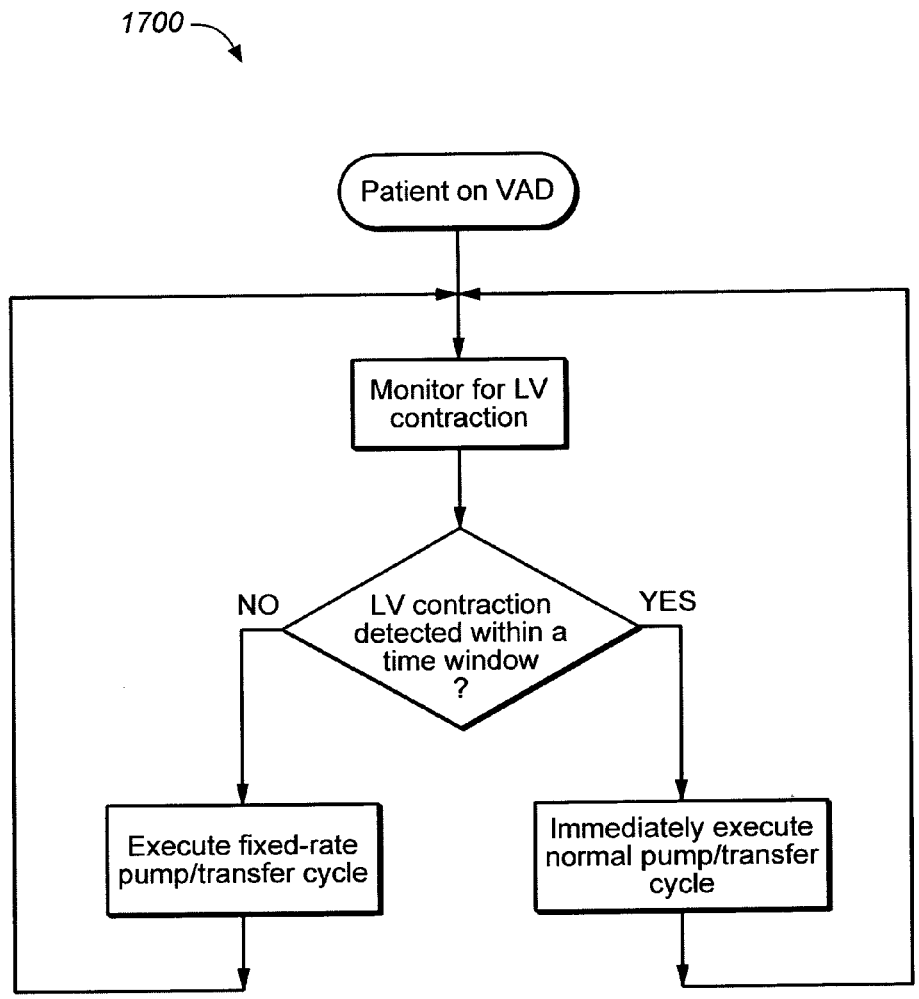
FIG. 17 is flowchart showing one embodiment method for the operation of the inventive pump during arrhythmia.

One embodiment of the present invention includes a blood pump having a control system for use during arrhythmias. Specifically, the schematic of FIG. 17 provides the required control by using an automatic mode switching approach 1700. The structure of the proposed device allows a more accurate determination of the actual physiological state (e.g., LV contraction), than non-pulsatile pumps. This allows the controller to sense abnormal physiological states and switch to alternative operating modes. The intent is to allow the device to maximize blood pumped through the arterial system, if and when the natural heart cannot pump blood (either partially or totally). This is especially important during periods of low blood volume (hypovolemic conditions), during electrical disturbances such as arrhythmias (including atrial, ventricular, and/or supraventricular arrhythmias) or periods of low ventricular contractility. The most important factor during these low flow conditions is to reduce the potential for perfusion deficit or thromboembolic events.

As shown in FIG. 17, the previously described method of detecting LV contraction is used for normal heart contractions, i.e., by detection of pusher-plate (armature) motion during the wait period following the transfer stroke. When LV contraction is detected, the device immediately executes a normal pumping cycle, i.e., a pump stroke followed by a transfer stroke. During normal physiologic conditions, detection of LV contraction should occur within a given time period following completion of the previous eject/transfer cycle. Conversely, failure to detect LV contraction within this time window is consistent with one of the abnormal physiologic states (hypovolemia, arrhythmia or low contractility) associated with poor heart function. If LV contraction is not detected within the expected time window, then a pump/transfer cycle will be triggered upon expiration of the time window. This ejection is in effect fixed-rate, occurring a set time after completion of the previous pump/transfer cycle. This effectively ensures a minimum allowable pump rate. Combined with the active filling inherent in this pump configuration, this algorithm measures a minimum level of pump output, reducing the potential harmful effects of arrhythmias and other low-flow conditions.

Sensors for the Control of Ventricular Assist System

The pumping of blood through ventricular assist system 22 results, in part, from current waveforms supplied to coils 207 as controlled by controller 40. The dynamics of pump

200 as described above can be controlled from signals indicating one or more of the following: the pressure in one or more of chambers 220, the position, velocity or acceleration of actuator plate 210, and the current through coils 207. In a preferred embodiment, pump 200 is controlled using sensors for the current of coil 207 and the position of actuator plate 210. Many techniques for measuring current are know in the field. The measurement of the position of the suspended actuator plate is preferably done without contact with the plate. Discussion of several techniques for measuring the position of the actuator plate and the pressure within the pump follows.

Actuator Plate Position Measurements

Several techniques for measuring the position of the actuator plate have been tested, including but not limited to load cells to measure the stress on springs 231, eddy current proximeters in or on frame 209 to detect the presence of magnets 601, a linear differential transformer (LVDT), analog-output Hall-effect sensors, and directly detecting field change caused by armature motion. Since there are no bearings or guides on armature 210, the armature can tilt during operation due to dynamic pressure gradients across chambers 220. Thus, at last two spring sensors, LVDT or eddy current sensors are required on opposite sides of armature 210 to obtain a correct position signal.

One position sensor of armature 210 measures the voltage across coils 207, and in particular changes in the voltage resulting from field changes due to armature motion on the drive circuit. Specifically, the drive coil voltage is given by:

$$V = IR + L \cdot dI/dt + kQ \qquad (11)$$

where I=coil current I, R=coil resistance, L=coil self-inductance L, and Q is the signed pump flow. Typically, kQ term is about 10 mV/(ml/sec), R is about 6 Ω and L=33 mH. The IR and L·dI/dt terms are compensated by analog circuitry in the electronics. Variation of coil resistance R with temperature and hence with pumping power can be accounted for by including a thermistor to measure coil temperature. The remaining output voltage, representing the kQ term, is integrated. The linearity of this technique is adequate for controlling pump 200.

Figure 13:
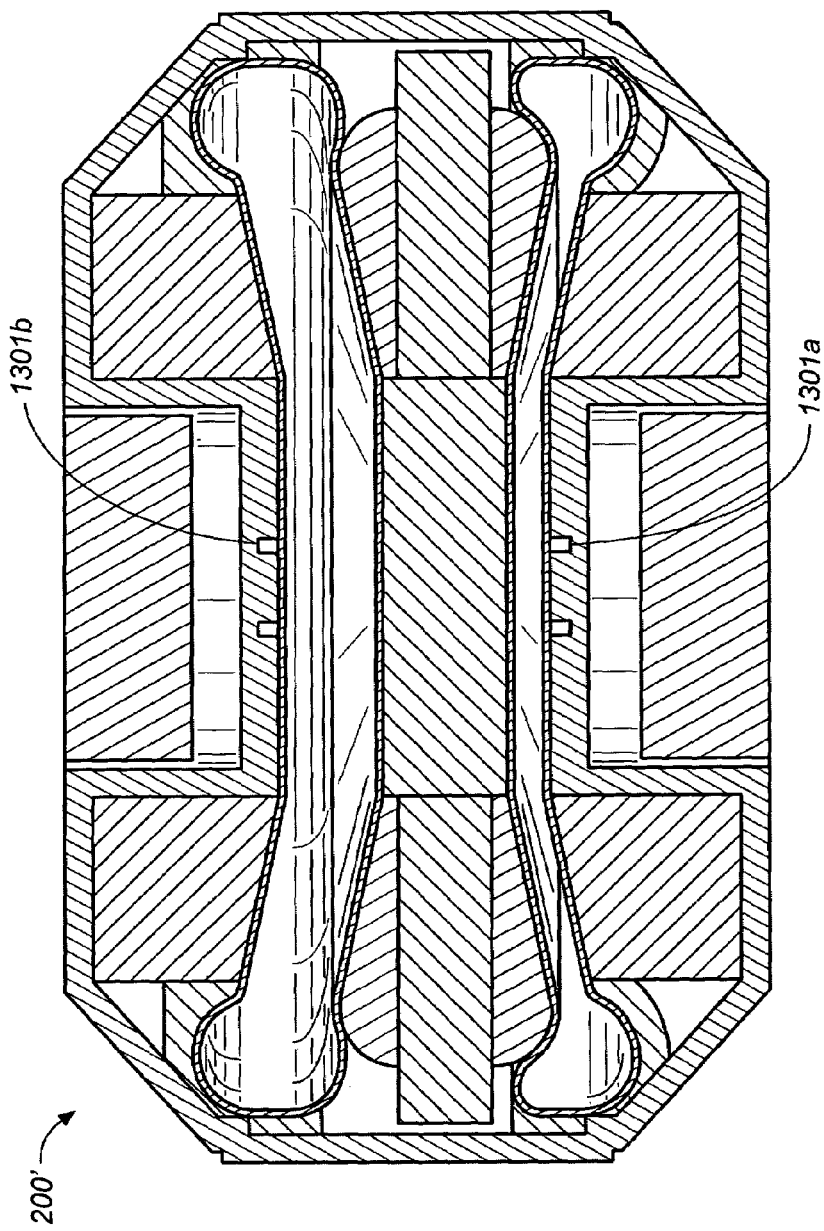
FIG. 13 is a sectional view of an embodiment of the pump showing the magnetic field sensor.

An alternative position detector embodiment is to measure the induced voltage in a coil added to frame 209. This is illustrated in FIG. 13 as a pair of small sensor coils 1301a and 1301b provided in an annular groove of a face of pole 801a' of pump 200'. Coils 1301 intercept only part of the magnetic flux determined solely by the geometry of pump 200'. The flow of current through coils 1301 is negligible, and so they can be wound with smaller wire with little dissipation. A fraction of the self-induced voltage (L·dI/dt term) is still present, but this is also determined purely by coil and pole geometry.

Since sensor coils 1301 respond to armature velocity they are ideal for their most critical function—detecting the start of motion of actuator plate 210' to initiate the pump stroke. To produce the pump volume waveform needed for cycle control, system monitoring, and calculating pump output, the velocity waveform must also be integrated. The endpoints must therefore also be determined to calibrate integrator zero and verify span. In principle this can be done directly by observing the abrupt change in velocity drop if and when the armature 210' hits armature stops 233' at the end of the pump stroke. For a multiyear design, it is preferred to minimize such impact which could cause wear, and wastes energy.

Several techniques are available to perform short-range end-of-stroke detection, also known as full-fill (FF) and full-eject (FE) sensing, and not shown in the figures. One alternative is to place short-range Hall sensors on the frame (also referred to herein as the stator) to sense the outer edges of the magnets 601. The sensors are placed in small notches in the stator, where they are shielded from the field until the corner of the magnet overlaps the notch. Again, the function is controlled by structural geometry, eliminating need for recalibration.

Though drive coil voltage cannot determine pump volume and flow as accurately as some other sensors, the voltage is easy to measure and is thus available as a backup or "failsafe" control signal in the event of sensor, electronics, or cable failure. Since the drive coil circuit must be intact to operate the VAD at all, it can be controlled whenever it can be operated. Specifically, the device can be operated with only two wires leading to pump 200.

In principle, all control functions can be accomplished using this signal alone, though control precision may degrade. As noted above, a steady coil current may be commanded during a "wait" interval to modify the eject assist pressure. During this interval, when the pump is not moving and the current is constant, the coil voltage is simply IR. Thus the slowly varying value of resistance can be measured and compensated for. Alternatively, a test current may be introduced solely for this purpose. The stroke endpoints may be determined by detecting the abrupt rate change as the pusher plate hits its end stops.

Pump Pressure Sensing

Under normal operating conditions, measurements of the position of actuator plate 210 and coil current I provide sufficient information to control pump actuation appropriately, responding to changes in preload (filling conditions, e.g. LV pressure) or afterload (aortic pressure). Since the force exerted on actuator plate 210 is a function of the coil current and net bias force, knowledge of the coil current I during the pump stroke provides an indication of the difference in pressure (ΔP) between the pre-chamber (the LV Pressure in chamber 220a) and pumping chamber (the aortic pressure in chamber 220b). Under certain circumstances, it might be beneficial to know the actual filling or ejecting pressures, not merely the difference between them. For instance, an abnormally high ΔP for a given eject rate could be the result of either an inflow conduit occlusion (causing an abnormally low filling pressure) or an outflow conduit occlusion (causing an abnormally high ejecting pressure). A measurement of either pressure, together with the ΔP value derived from the coil current during ejection, would provide values for the actual filling and ejecting pressures. This would allow a simple differentiation between, for instance, an inflow occlusion and an outflow occlusion. It would also facilitate response to extremely poor preload conditions. In particular, knowledge of a negative pressure within the pre-chamber or filling tract would provide a direct indication of inflow occlusion or inadequate preload.

Figure 14:
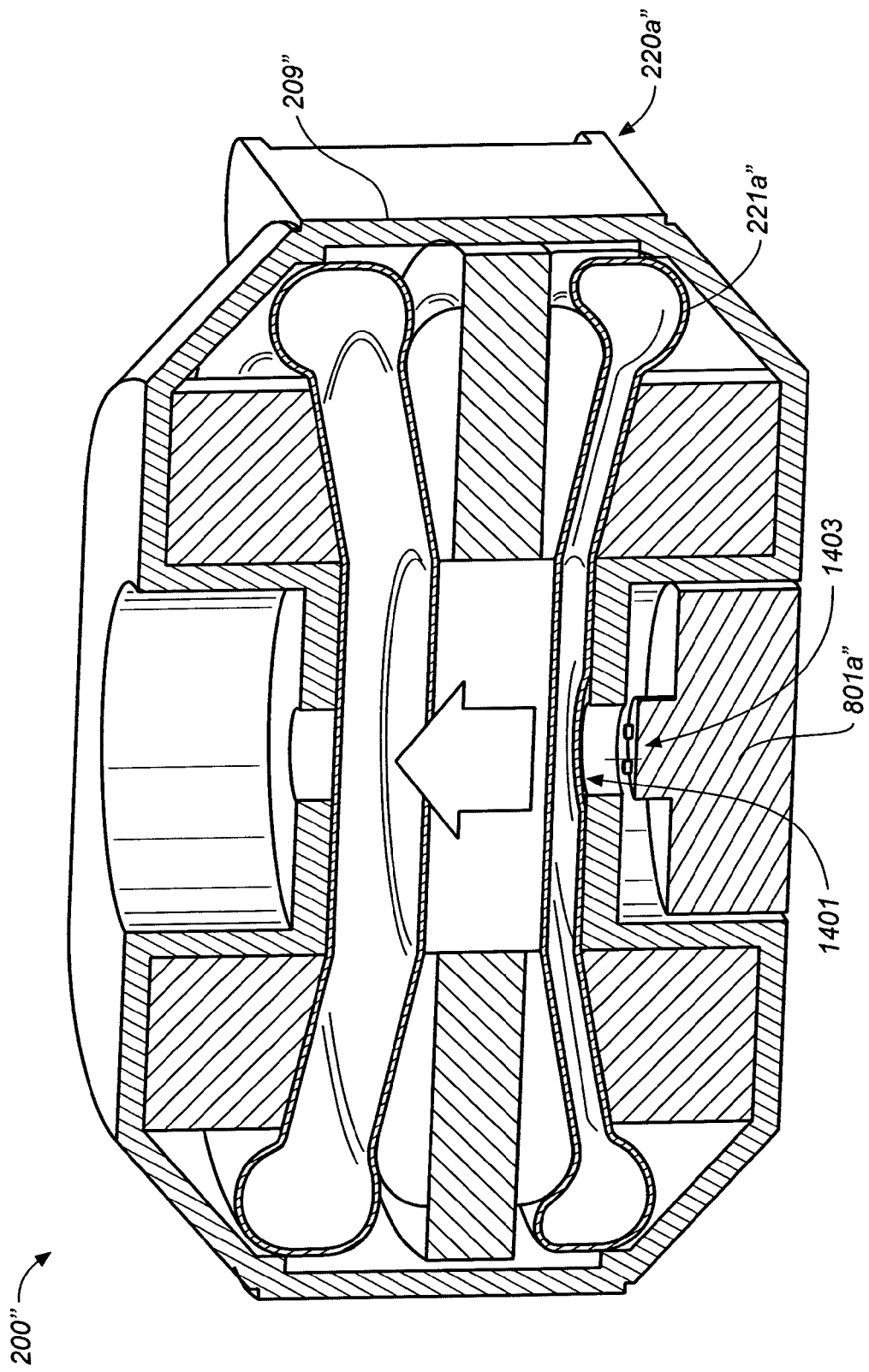
FIG. 14 is a sectional view of an embodiment of the pump showing an embodiment of a pressure sensor.

One possible means of pressure detection is shown in FIG. 14 for a pump 200". A region 1401 of pump sac 221a" is left unbonded to frame 209". The unbonded region 1401 may be over the pole 801a", as illustrated, or in any non-flexing portion of the pre-chamber, e.g., in its inflow or outflow port, or somewhere in the inflow conduit. A means is provided to detect deflection of the unbonded sac region, such as would occur if the pressure within the pre-chamber were to become negative. The motion is preferably detected by an optical sensor 1403 (e.g., an LED and photo-detector)

or any other appropriate means of detecting inward deflection of the sac. Thus, a negative pressure within the pre-chamber would be identified through detection of sac motion.

Alternative Pump Embodiments

Figure 15:
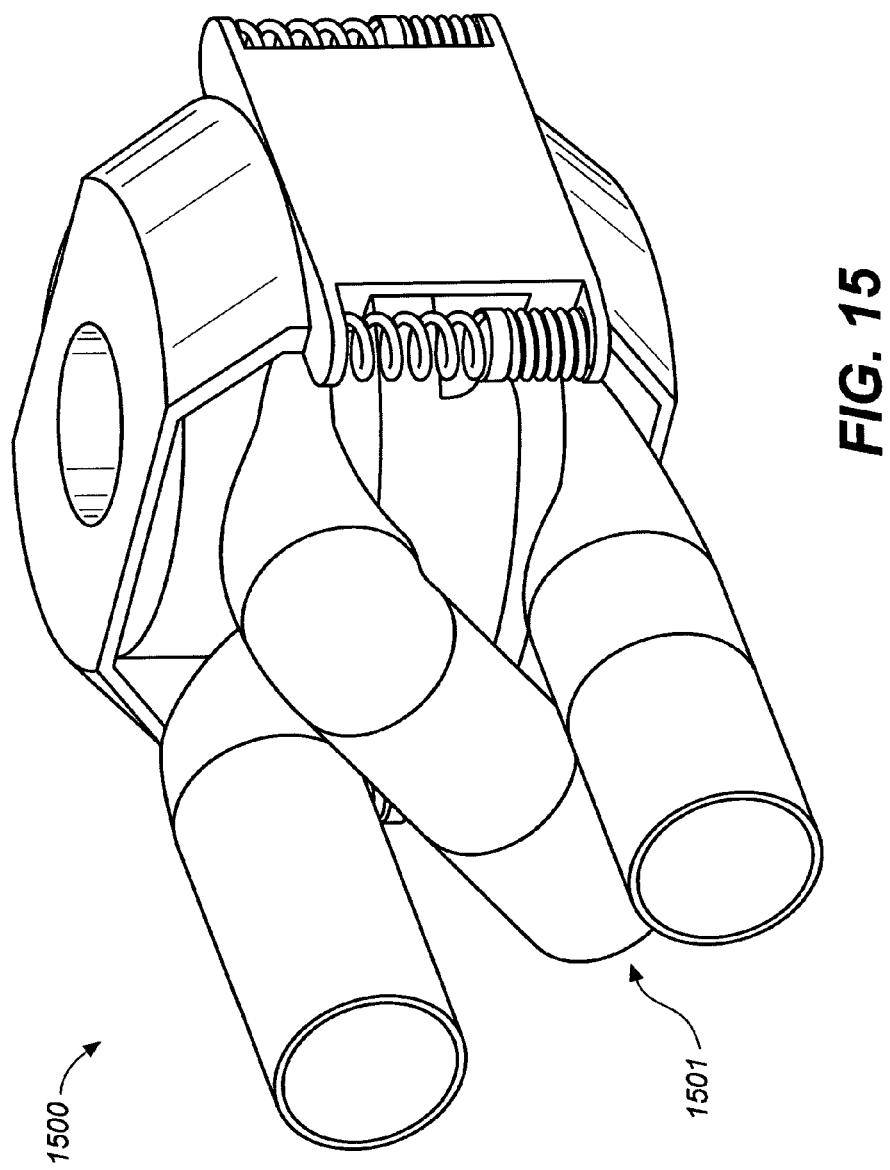
FIG. 15 is a perspective view of an alternative embodiment pump having an external transfer portion.
Figure 16:
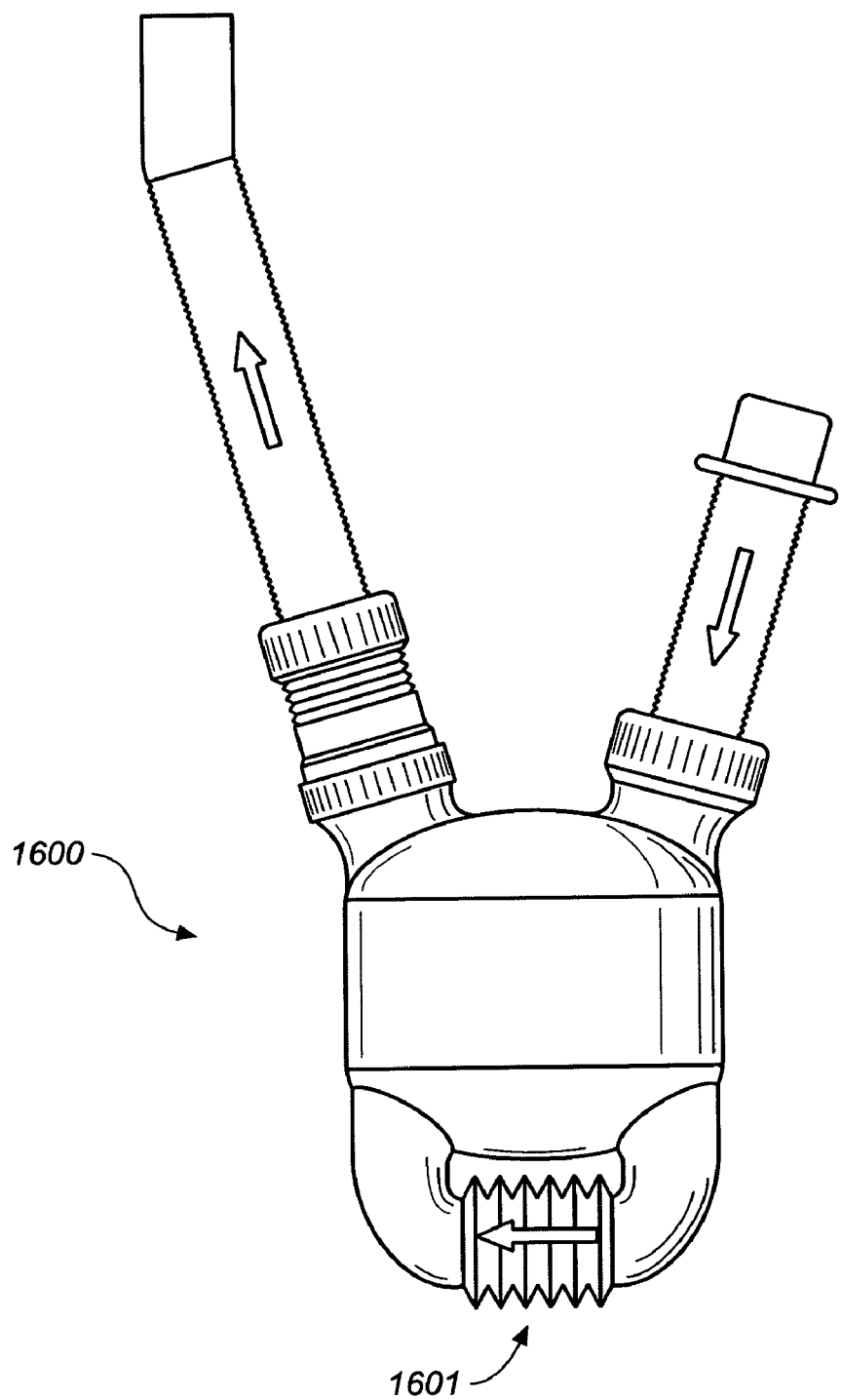
FIG. 16 is a plan view of an additional alternative embodiment pump having an external transfer portion.

The electromagnetic drive, spring suspension, control, and other aspects of the present invention can be incorporated into pump designs using two variable-volume chambers connected in series. In particular, series-displacement pumps have been described in the '60 patent. Thus for example, FIG. 15 shows pump 1500. Pump 1500 is a pump having the variable-volume chamber design of the series displacement pump of the '601 patent and the electromagnetic structure 800 of the present invention. Specifically, the transfer portion between the variable-volume chambers is provided by an external transfer portion 1501 that includes a one-way valve to control flow through the chambers. Another alternative embodiment is shown as pump 1600 in FIG. 16. Pump 1600 includes a transfer port 1601 on the side of pump 1600 opposite the blood inflow. Generally, the transfer port can be positioned at nearly any orientation relative the inflow and outflow, such as 90 degrees or any other convenient angle.

BVAD operation can be achieved using one of the two following embodiments. If the first BVAD embodiment, a patient P is provided with two separate pumps, a LVAD and a RVAD. These pumps are separately provided with net bias forces as described above for the right and left ventricles.

A second BVAD embodiment incorporates the electromagnetic structure 800 and the spring suspension of the present invention with the chamber valving of the BVAD pump configuration of the '601 patent. In the BVAD of the '601 patent, each of a pair of chambers has a pair of one-way valves. In the present invention, each chamber is adapted to pump one of the two ventricles. Since the pumping requirements of the two ventricles differ, with the left side having a higher pressure than the right, the bias force of the energy storage mechanism can be adjusted to load level the drive utilization. Specifically, the bias force is applied towards the chamber pumping from the left ventricle. This provides a much improved operation of the BVAD of that patent by providing a net bias force that favors the left ventricle. Specifically, when pumping the right ventricle, a portion of the electromagnetic drive energy is stored in the springs, and the pump delivers blood at a low pressure. When pumping the left ventricle, the electromagnetic drive energy is augmented by recovered spring energy to provide the higher pressure required by the left ventricle. The net bias force can thus be selected to load level the energy of the electromagnetic drive between the right and left pumping strokes.

The invention has now been explained with regard to specific embodiments. Variations on these embodiments and other embodiments may be apparent to those of skill in the art. It is therefore intended that the invention not be limited by the discussion of specific embodiments. It is understood that the examples and embodiments described herein are for illustrative purposes only and that various modifications or changes in light thereof will be suggested to persons skilled in the art and are to be included within the spirit and purview of this application and scope of the appended claims.

What is claimed is:

1. A ventricular assist device for pumping blood between an inlet and an outlet, said device comprising:
   an implantable frame;
   a pair of compressible chambers disposed within said frame, said pair of compressible chambers including a first chamber connected to the inlet and a second chamber connected to the outlet;
   an actuator disposed between said pair of compressible chambers and movable therebetween, where the movement of said actuator increases the volume of one of said pair of compressible chambers and decreases the volume of the other of said pair of compressible chambers;
   a one-way valve for providing fluid communication from said first chamber to said second chamber; and
   a drive unit adapted to alternately move said actuator towards one or the other of said pair of compressible chambers,
   wherein the movement of said actuator towards said first chamber is a transfer stroke that transfers said blood within said first chamber to said second chamber, and
   wherein the movement of said actuator towards said second chamber is a pump stroke that fills said first chamber from said inlet and empties said second chamber into said outlet.

2. The ventricular assist device of claim 1, wherein said one-way valve is a first one-way valve and further including a second one-way valve at the outlet of said second chamber to provide fluid communication from said second chamber to said outlet.

3. The ventricular assist device of claim 1, wherein said one-way valve is disposed within said actuator.

4. The ventricular assist device of claim 1,
   wherein said frame includes a soft magnetic material;
   wherein said actuator has an axis and includes a magnetic core about said axis and one or more magnets each having a pair of magnetic poles, a first pole and a second pole, oriented perpendicular to said axis with each of said first magnetic poles oriented either towards or away from said axis, and
   wherein said drive unit includes an electromagnetic drive including one or more coils disposed within said frame and an armature coupled to said actuator, wherein said electromagnetic drive, when energized, providing a force on said armature towards one or the other of said compressible chambers according to the magnetic interaction of said soft magnetic material, said one or more magnets, and the energization of said one or more coils.

5. The ventricular assist device of claim 4, wherein said actuator includes said armature.

6. The ventricular assist device of claim 4, said drive unit further including an energy storage element having one or more springs positioned between said frame and said armature to exert a spring force on said armature;
   wherein said one or more magnets generate a magnet force on said armature resulting from the attraction of said one or more magnets to said frame when said one or more coils is not electrically energized,
   wherein said one or more energized coils generates a coil force on said armature that is approximately independent of the position of said armature along said polar axis and that varies according to the degree of energization of said one or more coils.

7. The ventricular assist device of claim 6, wherein the sum of said spring force, said magnet force, and said coil force is approximately independent of the position of said armature along said polar axis, and varies according to the degree of energization of said one or more coils.

8. The ventricular assist device of claim 4,
wherein one or more pairs of gaps are defined between the armature and each one of said one or more pairs of poles, and
wherein the coil flux follows a path that contains therewithin said frame, said one or more pairs of poles, said one or more pairs of gaps, and said armature, and where each said magnet is substantially free of the coil flux.

9. The ventricular assist device of claim 8, wherein the coil flux follows a path including said frame, one pole of said one or more pair of poles, one gap of said one or more pair of gaps, said armature, another gap of said one or more pair of gaps, another pole of said one or more pair of poles, and said frame; and where each said magnet is substantially free of the coil flux.

10. A biventricular assist device comprising two ventricular assist devices of claim 1.

11. A ventricular assist device for pumping blood between an inlet and an outlet, said device comprising:
a pair of compressible chambers including a first chamber with a first volume and a second chamber with a second volume, where said first volume and said second volume are variable, and where the sum of said first volume and said second volume are approximately constant;
an actuator disposed between said pair of compressible chambers and movable to change said first and second volumes,
a drive unit for moving said actuator; and
a one-way valve for providing fluid communication from said first chamber to said second chamber,
wherein the movement of said actuator towards said first chamber decreases said first volume and is a transfer stroke that transfers said blood within said first chamber to said second chamber, and
wherein the movement of said actuator towards said second chamber decreases said second volume and is a pump stroke that fills said first chamber from said inlet and empties said second chamber into said outlet.

12. The ventricular assist device of claim 11, wherein said one-way valve is disposed in said actuator.

13. The ventricular assist device of claim 11, wherein said one-way valve is a first one-way valve, and further comprising a second one-way valve at the outlet of said second chamber to provide fluid communication from said second chamber to said outlet.

14. The ventricular assist device of claim 13, further including:
a frame substantially surrounding said pair of compressible chambers and including a soft magnetic material;
wherein said actuator comprises a magnetic core and one or more magnets;
wherein said drive unit is an electromagnetic drive including one or more coils disposed within said frame that, when electrically energized, each generates a magnetic flux defining a pair of poles having an axis; and
an armature coupled to said actuator, said one or more magnets having poles oriented perpendicular to said axis with like oriented pole aligned towards said axis,
wherein said movement of said actuator moves said core along said axis, and
wherein said electromagnetic drive provides a force on said armature towards one or the other of said compressible chambers according to the magnetic interaction of said soft magnetic material, said one or more magnets, and the energization of said one or more coils.

15. The ventricular assist device of claim 14, said drive unit further including an energy storage element including one or more springs positioned between said frame and said armature so as to exert a spring force on said armature;
wherein said one or more magnets generate a magnet force on said armature resulting from the attraction of said magnet to said frame when said one or more coils are not electrically energized,
wherein the sum of said spring forces and said magnetic force is a net bias force that is approximately independent of the position of said armature along said polar axis and biases said armature towards one of said pair of poles,
wherein said energized coils generate a coil force on said armature that is approximately independent of the position of said armature along said polar axis and that varies according to the degree of energization of said coils.

16. A biventricular assist device comprising two ventricular assist devices of claim 11.

17. A ventricular assist device for pumping blood between an inlet and an outlet, said device comprising:
a frame formed from a soft magnetic material;
a pair of compressible chambers disposed in said frame, where said pair of compressible chambers includes a first chamber connected to the inlet and a second chamber connected to the outlet;
an actuator disposed between said pair of compressible chambers and movable therebetween, where the movement of said actuator increases the volume of one of said pair of compressible chambers and decreases the volume of the other of said pair of compressible chambers;
a first one-way valve for providing fluid communication between said pair of chambers in a direction from said first chamber to said second chamber; and
a second one-way valve at the outlet of said second chamber for providing fluid communication from said second chamber to said outlet,
an electromagnetic drive disposed within said frame; and
an energy storage element disposed between said frame and said actuator,
wherein the motion of said actuator towards said first chamber is a transfer stroke that transfers said blood within said first chamber to said second chamber, and the motion of said actuator towards said second chamber is a power stroke that fills said first chamber from said inlet and empties said second chamber into said outlet;
wherein, during said transfer stroke, electric power delivered to said electromagnetic drive is stored in said energy storage element, and
wherein, during said power stroke, electric power delivered to said electromagnetic drive and said stored energy is delivered to said actuator.

18. The ventricular assist device of claim 17, wherein said first one-way valve is disposed within said actuator.

19. The ventricular assist device of claim 17, wherein said actuator has an axis and includes a magnetic core about said axis and one or more magnets having a first and second magnetic poles oriented perpendicular to said axis with each of the first magnetic poles oriented either towards or away from said axis,
wherein said electromagnetic drive includes one or more coils disposed within said frame and an armature coupled to said actuator, and wherein said electromagnetic drive, when energized, provides a force on said armature towards one or the other of said compressible chambers according to the magnetic interaction of said soft magnetic material, said one or more magnets, and the energization of said one or more coils.

20. The ventricular assist device of claim 19, wherein said armature is part of said actuator.

21. The ventricular assist device of claim 19, said energy storage element having one or more springs positioned between said frame and said actuator to exert a spring force on said actuator;
wherein said one or more magnets generates a magnetic force on said actuator resulting from the attraction of each said magnet to said frame when said one or more coils is not electrically energized,
wherein the sum of said spring forces and said magnetic force is a net bias force that is approximately independent of the position of said actuator along said polar axis and biases said actuator towards one of said pair of poles, and
wherein said energized coils generate a coil force on said actuator that is approximately independent of the position of said actuator along said polar axis and that varies according to the degree of energization of said coils.

22. The ventricular assist device of claim 19,
wherein one or more pairs of gaps is defined between the armature and each of said pair of poles, and
wherein the coil flux follows a path including one of said pair of poles, one of said pair of gaps, said armature, the other of said pair of gaps, and the other of said pair of poles, where the magnet is substantially free of the coil flux.

23. The electromagnetic drive of claim 19, wherein the coil flux follows a path including one of said one or more pair of poles, one of said one or more pair of gaps, said armature, the other of said one or more pair of gaps, and the other of said one or more pair of poles, where the magnet is substantially free of the coil flux.

24. A biventricular assist device comprising two ventricular assist devices of claim 17.

25. An electromagnetic drive comprising:
a frame formed from a soft magnetic material;
one or more coils disposed within said frame that, when electrically energized, generate a magnetic flux and define one or more pairs of magnetic poles each having a polar axis;
an armature within said frame having a magnetic core, a non-magnetic material surrounding said core, and one or more magnets in said non-magnetic material, wherein said core is movable along said polar axis, and where the poles of said one or more magnets are oriented perpendicular to said polar axis with like oriented pole aligned towards said polar axis; and
one or more springs positioned between said frame and said armature so as to exert a spring force on said armature;
wherein said one or more magnets generate a magnet force on said armature resulting from the attraction of said magnet to said frame when said pair of coils is not electrically energized,
wherein the sum of said spring forces and said magnetic force is a net bias force that is approximately independent of the position of said armature along said polar axis and biases said armature towards one of said pair of poles, and
wherein said energized coils generate a coil force on said armature that is approximately independent of the position of said armature along said polar axis and that varies according to the degree of energization of said coils.

26. The electromagnetic drive of claim 25,
wherein one or more pair of gaps is defined between the armature and each one of said one or more pair of poles.

27. A drive system for a pump including a first variable volume chamber, a second variable volume chamber, one or more magnets, and an actuator movably disposed between said first and second chambers, where the movement of said actuator changes the volume of said first chamber and said second chamber, said system comprising:
an electromagnetic drive including an electromagnet and an armature coupled to said actuator; and
an energy storage device that biases said actuator to decrease the volume of said second chamber, where said energy storage device stores energy from said armature when said armature moves to decrease the volume of said first chamber, and where said energy storage device delivers energy to said armature when said armature moves to decrease the volume of said second chamber.

28. A ventricular assist device comprising:
a blood pump connected to a heart and adapted to pump blood from a ventricle to the aorta;
said pump including a pair of compressible chambers disposed in said frame, where said pair of compressible chambers including a first chamber connected to the inlet and a second chamber connected to the outlet;
a drive system to supply power to said pump;
a sensor that detects a negative pressure within said first chamber; and
a controller triggered by an output of said sensor for actuating said blood pump.

29. The ventricular assist device of claim 28, where said controller has a programmable actuating algorithm for changing said actuating from one beat of the heart to the next beat.

30. A ventricular assist device comprising:
a blood pump connected to a heart and adapted to pump blood from a ventricle to the aorta;
a drive system to supply power to said pump;
a sensor that detects changes in the verticular pressure; and
a controller triggered by an output of said sensor for actuating said blood pump,
such that said sensor triggers said controller based on the sensing of changes in the ventricular pressure;
wherein said pump includes an actuator plate and said triggering is based on the motion of said actuator plate due to variations in ventricular pressure;
wherein said actuator plate is between a pair of serially connected pumping chambers in said pump that operates in a two-stroke mode, specifically a power stroke and a transfer stroke, said pump includes a spring bias for storing energy from a drive unit during the transfer stroke so as to reduce pump size and reduce electrical energy consumption of said pump.

31. The ventricular assist device of claim 30, wherein said pump is triggered from variations in the ventricular pressure such that said pump may execute a pump/transfer stroke sequence at more or less than the cardiac cycle.

32. The ventricular assist device of claim 30, wherein said sensor detects contractions of the left ventricular of a heart under normal heart conditions and triggers said controller.

33. A biventricular assist device comprising:
- an electromagnetic drive including one or more coils disposed within a frame that, when electrically energized, generate a magnetic flux and define one or more pairs of magnetic poles each having a polar axis; and an armature having an axis and includes a magnetic core about said axis, one or more magnets having first and second magnetic poles oriented perpendicular to said axis with each of the first magnetic poles oriented either towards or away from said axis,
- a pair of compressible chambers, each adapted to pump one of the right and left ventricle according to the action of said electromagnetic drive; and
- an energy storage element adapted to store and release energy from said electromagnetic drive and said pair of compressible chambers,
- wherein, during a stroke to pump the right ventricle, electric power delivered to said electromagnetic drive is stored in said energy storage element, and
- wherein, during a stroke to pump the left ventricle, electric power delivered to said electromagnetic drive and said stored energy is delivered to said armature; and
- wherein said electromagnetic drive, when energized, provides a force on said armature towards one or the other of said compressible chambers according to the magnetic interaction of said frame, said one or more magnets, and the energization of said one or more coils.

34. A ventricular assist device comprising:
- a pair of compressible chambers connected in series, where said pair of compressible chambers includes a first chamber connected to the device inlet and a second chamber connected to the device outlet;
- an armature movable to contract one of said pair of chambers and expand the other of said pair of chambers;
- at least one, one-way valve providing fluid communication between said pair of chambers in a direction from said first chamber to said second chamber, where the motion of said armature towards said first chamber is a transfer stroke that transfers blood within said first chamber to said second chamber, and where the motion of said armature towards said second chamber is a power stroke that fills said first chamber from said inlet and empties said second chamber into said outlet;
- an electromagnetic drive; and
- an energy storage element coupled to said armature,
- wherein, during said transfer stroke, electric power delivered to said electromagnetic drive is stored in said energy storage element, and
- wherein, during said power stroke, electric power delivered to said electromagnetic drive and said stored energy is delivered to said armature.

35. A method of pumping blood with a ventricular assist device using a pump having two variable volume chambers including a first chamber to accept said blood at a pump inlet, a second chamber to expel said blood at a pump outlet, and a one-way valve between said first chamber and said second chamber to allow blood to flow from said first chamber to said second chamber, said method comprising:
- simultaneously increasing the volume of said first chamber and decreasing the volume of said second chamber with said one-way valve closed during a pump stroke;
- rapidly terminating said pump stroke such that the momentum of blood in the inflow conduit and outflow conduit and pump causes said one-way valve to open, such that the volume of blood discharged during said pump stroke is greater than the change in volume of said second chamber during said pump stroke.

36. The method of claim 35, wherein said one-way valve is a first one-way valve and said ventricular assist device further includes a second one-way valve at the outlet of said second chamber to provide fluid communication from said second chamber to said outlet.

37. The method of claim 35, wherein said pump has an active filling capability such that said pump can maintain a minimum level of circulation under abnormal heart conditions.

* * * * *